(12) United States Patent
Frazer et al.

(10) Patent No.: US 11,163,094 B2
(45) Date of Patent: Nov. 2, 2021

(54) SYSTEMS AND METHODS FOR ESTIMATING RESERVOIR STRATIGRAPHY, QUALITY, AND CONNECTIVITY

(71) Applicant: CHEVRON U.S.A. INC., San Ramon, CA (US)

(72) Inventors: Miles Ashley Frazer, Houston, TX (US); Kaveh Ghayour, Houston, TX (US)

(73) Assignee: CHEVRON U.S.A. INC., San Ramon, CA (US)

(*) Notice: Subject to any disclaimer, the term of this patent is extended or adjusted under 35 U.S.C. 154(b) by 573 days.

(21) Appl. No.: 16/115,391

(22) Filed: Aug. 28, 2018

(65) Prior Publication Data
US 2020/0073012 A1    Mar. 5, 2020

(51) Int. Cl.
*G01V 99/00* (2009.01)
*G01N 15/08* (2006.01)
*G01N 33/24* (2006.01)

(52) U.S. Cl.
CPC .......... *G01V 99/005* (2013.01); *G01N 15/08* (2013.01); *G01N 33/24* (2013.01); *G01V 2210/6122* (2013.01); *G01V 2210/6244* (2013.01); *G01V 2210/6246* (2013.01); *G01V 2210/64* (2013.01); *G01V 2210/661* (2013.01); *G01V 2210/74* (2013.01)

(58) Field of Classification Search
CPC ......... G01V 99/005; G01V 2210/6122; G01V 2210/74; G01V 2210/6246; G01V 2210/64; G01V 2210/661; G01V 2210/6244; G01N 15/08; G01N 33/24; G06F 30/00

USPC ....................................................... 703/10, 6
See application file for complete search history.

(56) References Cited

U.S. PATENT DOCUMENTS

| 2002/0099504 | A1* | 7/2002 | Cross ..................... G01V 11/00 702/2 |
| 2007/0219725 | A1 | 9/2007 | Sun |
| 2010/0223039 | A1 | 9/2010 | Maliassov |

(Continued)

OTHER PUBLICATIONS

Santos, Isaac, R. et al., "The Driving Forces of Porewater and Groundwater Flow in Permeable Coastal Sediments: A Review", Nov. 10, 2011, Estuarine, Coastal and Shelf Science 98, Elsevier, Ltd. (Year: 2011).*

(Continued)

*Primary Examiner* — Cedric Johnson
(74) *Attorney, Agent, or Firm* — Esplin & Associates, PC

(57) ABSTRACT

Exemplary implementations may: obtain, from the electronic storage, geological data corresponding to the geographic volume of interest; generate a framework for sediment deposition using a first set of multiple physical, chemical, biological, and geological processes; generate a framework for diagenesis using a second set of multiple physical, chemical, biological, and geological processes; generate a representation of sediment deposition by applying the geological data corresponding to the geographic volume of interest to the framework for sediment deposition; generate a representation of diagenesis based on the framework for diagenesis and the representation of sediment deposition; and display the representation of sediment deposition and the representation of diagenesis on a graphical user interface.

19 Claims, 23 Drawing Sheets
(21 of 23 Drawing Sheet(s) Filed in Color)

(56) References Cited

U.S. PATENT DOCUMENTS

| | | | |
|---|---|---|---|
| 2011/0264430 A1* | 10/2011 | Tapscott | G01V 99/00 703/10 |
| 2014/0163883 A1 | 6/2014 | Granjeon | |
| 2018/0021732 A1* | 1/2018 | Osmundson | B01D 63/082 210/321.6 |
| 2018/0031732 A1 | 2/2018 | Mosse | |
| 2018/0347321 A1* | 12/2018 | Hamon | E21B 49/00 |

OTHER PUBLICATIONS

Cai-Neng, Zou et al., "Genesis, Classification, and Evaluation Method of Diagenetic Facies", Oct. 2008, Petroleum Exploration and Development, vol. 35, Issue 5, Science Direct. (Year: 2008).*

PCT International Search Report and Written Opinion, International Application No. PCT/US2019/045469, dated Oct. 15, 2019 (11 pages).

Smart, Peter L. et al., A New Forward Simulation Model for Sedimentary Architecture and Near-Surface Diagenesis in Isolated Carbonate Platforms; CARB3D; American Association of Petroleum Geologists. International Meeting, Paris, abstracts. 2005 (1 page).

Dionisos: a model of multiple resources; Science@ifpen; http://www.ifpenergiesnouvelles.com/Expertise/Research-divisions/Geosciences/Dionisos-a-model-of-multiple-resources; Issue 22—Sep. 2015 (4 pages).

Geological Process Modeling Software for Improved Reservoir Prediction; Eage Daily News; Eage Conference & Exhibition; 2017 ; Schumberger GPM: https://www.software.slb.com/products/gpm (1 page).

* cited by examiner

SYSTEMS AND METHODS FOR ESTIMATING RESERVOIR STRATIGRAPHY, QUALITY, AND CONNECTIVITY

FIELD OF THE DISCLOSURE

The present disclosure relates to systems and methods for estimating reservoir stratigraphy, quality, and connectivity.

BACKGROUND

Existing reservoir models may provide inaccurate estimates of reservoir quality and connectivity. These models are based on limited data, overly rely on successful reservoirs, and/or other reasons. For example, data collection is often focused on increased or improved sampling, instead of a better understanding of the processes that drive sedimentary deposition and fundamentally control their internal heterogeneity. This only provides incremental refinements to the estimates of reservoir quality and connectivity because even the most rigorous sampling will record only a small fraction of 1% of the data available in a particular reservoir volume. Moreover, this sampling is usually focused on successful reservoirs, improperly biasing the accuracy of existing models. The inaccuracy of these models is highlighted in carbonate reservoirs, where heterogeneity in reservoir properties can be more dramatic, due to the complex interactions of both depositional and diagenetic processes during their formation.

SUMMARY

An aspect of the present disclosure relates to a method. The method may include obtaining, from the electronic storage, geological data corresponding to the geographic volume of interest. The method may include generating a framework for sediment deposition using a first set of multiple physical, chemical, biological, and geological processes. The method may include generating a framework for diagenesis using a second set of multiple physical, chemical, biological, and geological processes. The method may include generating a representation of sediment deposition by applying the geological data corresponding to the geographic volume of interest to the framework for sediment deposition. The representation of sediment deposition may indicate a change to an amount of sediment in the geographic volume of interest as a function of position and time. The method may include generating a representation of diagenesis based on the framework for diagenesis and the representation of sediment deposition. The representation of diagenesis may indicate a change in porosity and permeability as a function of position and time. The method may include displaying the representation of sediment deposition and the representation of diagenesis on a graphical user interface.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

The technology disclosed herein, in accordance with one or more various implementations, is described in detail with reference to the following figures. The drawings are provided for purposes of illustration only and merely depict typical or example implementations of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
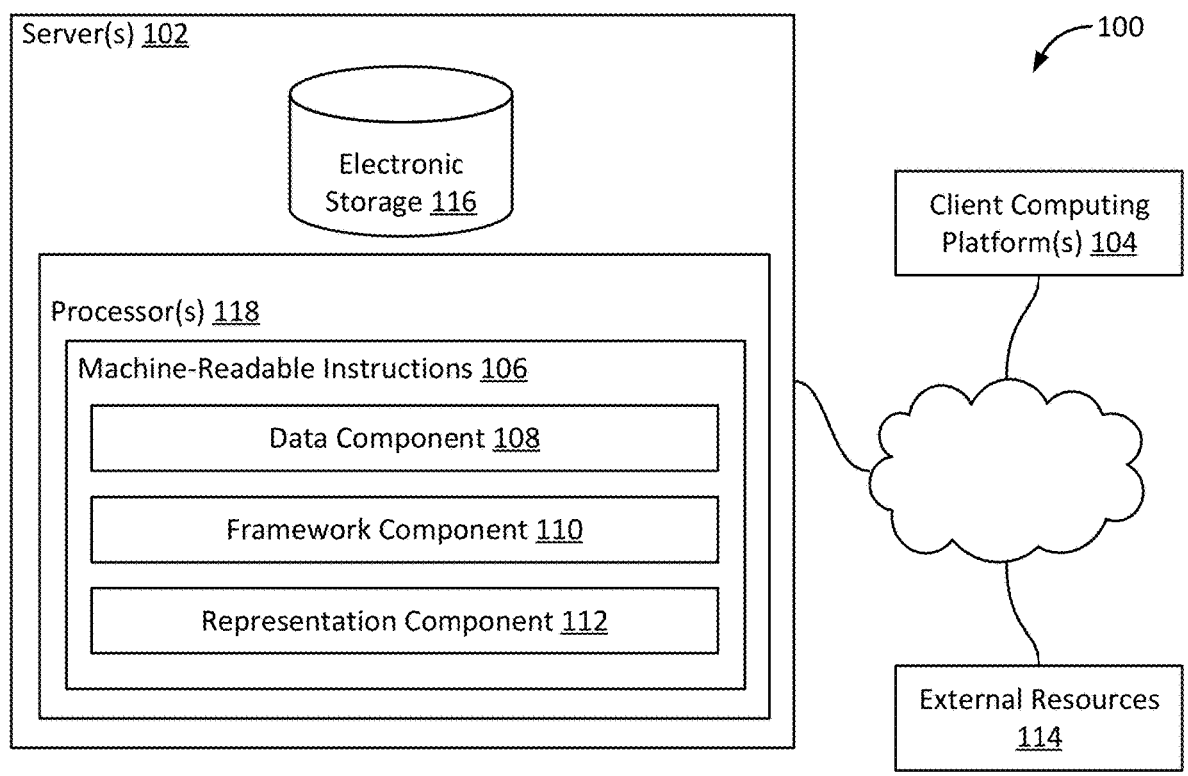
FIG. 1 shows a system configured to estimate reservoir stratigraphy, quality, and connectivity, in accordance with one or more implementations.

Systems and methods configured to estimate reservoir stratigraphy, quality, and connectivity in a geographic volume of interest are disclosed. Physical, chemical, biological, and geological processes may be used to estimate reservoir stratigraphy, quality, and connectivity and reservoir properties in a geographic volume of interest. Geological data corresponding to the geographic volume of interest may be obtained. A framework for sediment deposition using a first set of multiple physical, chemical, biological, and geological processes may be generated corresponding to how sediment is deposited in the geographic volume of interest. A framework for diagenesis using a second set of multiple physical, chemical, biological, and geological processes may be generated to estimate how reservoir-critical rock properties change after sediment deposition. In implementations, representations based on the two sets of chemical, physical, and geological concepts may be generated to simulate the processes that occur to generate a stratigraphic succession and its internal distributions of reservoir-critical rock properties. Changes to the amount of sediment deposited in the geographic volume of interest and how sediment changes in the simulation may be represented as a function of position and time.

As used herein, framework means a first set of physical, chemical, biological, and geological equations, processes, reactions, etc. that may govern how sediment is deposited and a second set of physical, chemical, biological, and geological equations, processes, reactions, etc. to estimate how rock properties may change after sediment deposition. In embodiments, the first set of physical, chemical, biological, and geological equations, processes, reactions, etc. and the second set of physical, chemical, biological, and geological equations, processes, reactions, etc. may be the same or a similar set of equations. As used herein, representation means a visualization of the framework after initial conditions and/or geological data has been input into a framework. The representation may provide visualizations of how deposition changes in a geographic volume of interest as a function of time and position. The representation may provide visualizations of how rock properties change after sediment deposition as a function of time and position. It should be appreciated that the representation may be a four-dimensional visualization, a three-dimensional visualization, a two-dimensional visualization, or any other type of visualization.

The multiple physical, chemical, biological, and geological processes may be used to determine the precipitation of carbonate sediment, such as oolitic sands, coral fragments, algal skeletons, and others, from seawater. Carbonate minerals, that make up carbonate rocks, may be chemically reactive. Carbonate sediment may be deposited as sea level rises and falls over time, creating sand flats, and sometimes islands. In some implementations, as sea level rises over the island, more sediment may be deposited onto the island. As sediments become buried, additional chemical, physical, and geological processes may be used to determine rock compaction and chemical alteration (e.g., diagenesis) of the buried sediment to form rock volumes.

As islands form from the sediment, the islands may be susceptible to diagenesis as fluids of different chemical composition (e.g., rain) flow through them as the local hydrology evolves alongside other geological developments. The diagenesis can dissolve areas of the carbonate rock, creating porous rocks capable of holding and flowing larger quantities of fluids (e.g., oil, gas, water, and/or other fluids) or can create caves which can be dangerous obstacles during drilling. Diagenesis may lead to growth of more calcium carbonate, such that pores in the carbonate rock may become clogged, preventing the storage and flow of fluids. The carbonate pore structures within the rock volume may be reorganized due to diagenetic processes. As a result, reservoir heterogeneity may be estimated from the representations simulating deposition and diagenesis using the multiple physical, chemical, biological, and geological processes.

FIG. 1 illustrates a system, in accordance with one or more implementations. In some implementations, system 100 may include one or more servers 102. Server(s) 102 may be configured to communicate with one or more client computing platforms 104 according to a client/server architecture and/or other architectures. Client computing platform(s) 104 may be configured to communicate with other client computing platforms via server(s) 102, according to a peer-to-peer architecture, and/or other architectures. Users may access system 100 via client computing platform(s) 104.

Server(s) 102 may be configured by machine-readable instructions 106. Machine-readable instructions 106 may include one or more instruction components. The instruction components may include computer program components. The instruction components may include one or more of a data component 108, a framework component 110, a representation component 112, and/or other instruction components.

Data component 108 may be configured to obtain, from the electronic storage, geological data corresponding to the geographic volume of interest. In some implementations, geological data may include light data, abiotic data, biotic data, fluid data, temperature data, sediment data, climate data, rainfall data, temperature data, soil data, water table data, sea level data, tide data, salinity data, ocean alkalinity data, carbon content data, nuclei data, dissolution data, oxidation data, equilibrium constants, porosity data, permeability data, and/or other data. The geological data may affect sediment deposition, precipitation, diagenesis, total carbon data, and/or other processes. For example, the precipitation of carbonate minerals may be mainly driven by heating, degassing of $CO_2$, and photosynthesis. It will be appreciated that the precipitation of carbonate materials may be driven by additional factors.

In implementations, a geographic volume of interest may be a body of water, bodies of land, atmosphere, and/or other geographic volumes of interest on Earth where sediment may be deposited. The geographic volume of interest may be a depositional system, such as a fluvial, deltaic, marine, lacustrine, eolian, and/or other systems. The geographic volume of interest may be on the scale of meters, tens of meters, hundreds of meters, thousands of meters, tens of kilometers, thousands of kilometers, and/or other distances.

Framework component 110 may be configured to generate a framework for sediment deposition using a first set of multiple physical, chemical, biological, and geological processes. In some implementations, a framework for sediment deposition may correspond to how sediment may be deposited in a geographic volume of interest including a sediment source, depositional processes, location, climate, and/or other features. The sediment source may include chemical precipitation and/or sediment from seawater, fluids, mountains, and/or other sources. Depositional processes may include deposition by wind, water, ice, and/or other processes. The location and/or climate may be a desert, swamp, river, island, and/or other geographic volumes of interest. Sediment may be deposited when the fluid flow can no longer transport the sediment. The framework for sediment deposition may illustrate lateral heterogeneity of the geographic volume of interest.

In some implementations, the framework for sediment deposition may be a combination of physical, chemical, biological, and geological equations, concepts, and/or processes, and how they may interact with each other to deposit sediment in a geographic volume of interest. In some implementations, one of the first set of multiple physical, chemical, biological, and geological processes may define its own equilibrium and may be dependent on boundary conditions.

In implementations, the first set of multiple physical, chemical, biological, and geological processes may include sedimentary precipitation processes, physical transport processes, and/or other physical, chemical, biological, and geological processes. The first set of multiple physical, chemical, biological, and geological processes may correspond to how seawater is directed towards oversaturation with respect to minerals.

In some implementations, sedimentary precipitation processes may be the equations, concepts, and/or processes corresponding to the formation of a solid mineral in a fluid. In implementations, precipitation may occur based on chemical reactions between two or more ions in solution, based on the changing temperature of ocean water, and/or other events. In some implementations, precipitation occurs between calcium cations and carbonate anions to form calcium carbonate. In implementations, calcium and carbonate in the ocean may be sourced from mountains, being dissolved in surface waters that flow to the ocean instead of being transported to a location as solid particles or grains (e.g., clastic sediment). Tide data and corresponding processes may affect sedimentary precipitation processes and the framework for sediment deposition because the tide recirculates the sea water through developed channels, driving sediment production.

In implementations, physical transport processes may include equations, concepts, and/or processes corresponding to the movement of sediment through currents, tides, flow of liquid, wind, ice, gravitational forces, and/or other mechanisms.

In some implementations, chemical saturation may represent the propensity for a solution to dissolve or precipitate a mineral under a set of conditions. When a solution is undersaturated with regards to a mineral it may dissolve the mineral. When a solution is oversaturated, it can no longer carry the mineral in the solution and may precipitate the mineral into a solid form. For example, when seawater is gradually evaporated, the solution evolves from being undersaturated to being oversaturated with respect to NaCl. Once the solution becomes oversaturated, solid crystal particles of sea salt (NaCl) form. The same chemical process may occur for calcium carbonate under various conditions.

Framework component 110 may be configured to generate a framework for diagenesis using a second set of multiple physical, chemical, biological, and geological processes. In some implementations, diagenesis may be the physical, chemical, biological, geological, and/or other environmental processes where the mineral constituents of a rock volume, or the sediment, become subject to chemical reactions. In some implementations, this may occur at relatively low temperatures and pressures. In some implementations, the mineral constituents may become involved in chemical reactions with the various waters, fluids, and/or other materials that flow through them. After undergoing diagenesis, the sediment may have different mineralogy, texture, and/or other features than the original sediment that was deposited at the location. The sediment may be compacted as they are buried beneath other layers of sediment and cemented by precipitated minerals. Parts of the sediment may be replaced by other minerals during diagenesis. The chemical reactions can change the size, shape, chemical composition, and/or other features of the rock composition.

In implementations, the framework for diagenesis may be based on output from the framework for sediment deposition. In implementations, the first set of multiple physical, chemical, biological, and geological processes may be different from the second set of multiple physical, chemical, biological, and geological processes. The second set of multiple physical, chemical, biological, and geological processes may include at least one of the first set of multiple physical, chemical, biological, and geological processes and apply at least one of the first set multiple physical, chemical, biological, and geological processes to rock volumes, settled sediment, and/or other sediment subject to diagenesis. In some implementations, the framework for diagenesis may be a combination of the second set of multiple physical, chemical, biological, and geological processes, and how they may interact with each other in the geographic volume of interest to affect diagenesis and generate rock volumes. In implementations, the rock volumes may be preserved, such that the structure of the rock volume is semi-permanent. In some implementations, one of the second set of multiple physical, chemical, biological, and geological processes may define its own equilibrium and may be dependent on boundary conditions In some implementations, the second set of multiple physical, chemical, biological, and geological processes may include a groundwater circulation model, a chemically reactive groundwater model, and/or other processes. In some implementations, the second set of multiple physical, chemical, biological, and geological processes may be a coupled model. In some implementations, the coupled model may use output from the groundwater circulation model as input for the reactive groundwater model or vice versa. In implementations, the coupled model may pass outputs as inputs between the models multiple times.

In some implementations, the groundwater circulation model may include the equations, concepts, and/or processes corresponding to the reorganization of pore structures in the rock volume. For example, this may include fluid interaction with the rock volume, composition of the rock volume, output from the framework for sediment deposition and representation of sediment deposition, and/or other processes.

In some implementations, the reactive groundwater model may include the equations, concepts, and/or processes corresponding to diagenesis and/or chemical solute transport. In some implementations, the reactive groundwater model may be based on modifications of porosity (i.e., available internal space for fluids) and permeability (i.e., pathways available for fluid movement), due to chemical reactions between groundwater and the rock volume. In some implementations, the reactive groundwater model may solve equations of, and illustrate, fluid flow through porous media, as well as chemical reactions between the fluid and the rock.

In implementations, the second set of multiple physical, chemical, biological, and geological processes corresponds to solving chemical equations, which may include, for example, equilibrium constants for calcite precipitation and dissolution, carbon dioxide dissolution, pH calculations, organic matter oxidation, and/or other equations, concepts, and processes. The chemical reactions would add or remove minerals to the rocks and change the porosity and/or permeability.

In some implementations, the second set of multiple physical, chemical, biological, and geological processes corresponds to spatial rules for the modification of porosity and permeability away from hydrological boundaries (e.g., a water table). Based on geological data, such as rainfall, presence of soil, local temperatures, and/or other data, the spatial rules may indicate porosity and permeability changes to the rock volume as a function of time.

Representation component 112 may be configured to generate a representation of sediment deposition by applying the geological data corresponding to the geographic volume of interest to the framework for sediment deposition. The representation of sediment deposition may indicate a change to an amount of sediment in the geographic volume of interest as a function of position and time. The representation of sediment deposition may indicate the change through visual effects on a graphical user interface. The visual effects may include color, location of objects (e.g., sediment, water, etc.), perspective of objects, scale of objects, markers, and/or other visual effects. The time may be on the scale of hours, day, months, years, decades, centuries, and/or other lengths of time.

The representation of sediment deposition may dynamically simulate changes to the geographic volume of interest based on the conditions imposed by the framework for sediment deposition (e.g., first set of multiple physical, chemical, biological, and geological processes). For example, the geographic volume of interest may include a shoal in a first location. When the data corresponding to the geographic volume of interest is applied to the framework for sediment deposition, the representation of sediment deposition may be generated. At a first time, the representation of sediment deposition may display the shoal. At a second time, the representation of sediment deposition may display sediment depositing in a second location as a function of position and time and a channel forming between the first location and the second location. At a third time, the representation of sediment deposition may display sediment forming a sand flat at the second location. Using the graphical user interface, the user may change the time at various intervals, as described above, to simulate the sedimentary effects of the environment on the geographic volume of interest based on the framework for sediment deposition.

Representation component 112 may be configured to generate a representation of diagenesis based on the framework for diagenesis and the representation of sediment deposition. The representation of diagenesis may indicate a change in porosity and permeability as a function of position and time. The representation of diagenesis may include one or more rock volumes formed from the sediment deposited in the representation of sediment deposition. The representation of diagenesis may indicate the change in the rock volume using visual effects, as described above. In implementations, the change in the rock volume corresponds to a change in shape, size, chemical composition of mineral components, petrophysical properties, and/or other changes within the rock volume.

The representation of diagenesis may dynamically simulate changes to the geographic volume of interest based on the conditions imposed by the framework for diagenesis (e.g., second set of multiple physical, chemical, biological, and geological processes). The representation of diagenesis may analyze the geographic volume of interest to determine a diagenetic region of interest. The diagenetic region of interest may include a region where rock properties may change. In some implementations, the diagenetic region of interest may be user selected, based on the multiple physical, chemical, biological, and geological processes corresponding to the water table location and/or other hydrological interface locations. In implementations, the diagenetic region of interest is determined based on the flow and transport of chemical reactants through the sediment and by tracking the balance of the reactants between water and rock as it moves through the rock.

Continuing the example above, the representation of diagenesis may incorporate output of the representation of sediment deposition. At the third time, the representation of diagenesis may determine diagenesis may occur at the sand flat at the second location. The representation of diagenesis may display changes to the rock properties of the sediment as a function of time. At a fourth time, the representation of diagenesis may display how the sand flat connectivity and quality changes based on the changes to the rock properties of the sediment. At the fourth time, the representation of diagenesis may determine diagenesis may occur around the shoal at the first location. At a fifth time, the representation of diagenesis may display how the sand flat connectivity and quality changes compared to the fourth time and how the sediment surrounding the shoal changes connectivity and quality based on the changes to the rock properties of the sediment surrounding the shoal. Using the graphical user interface, the user may change the time at various intervals, as described above, to simulate the effects of the environment on the geographic volume of interest based on the framework for diagenesis.

Representation component 112 may be configured to display the representation of sediment deposition and/or the representation of diagenesis on a graphical user interface. In implementations, the graphical user interface may include visual effects to illustrate changes to the representation of sediment deposition and/or the representation of diagenesis as a function of position and time. The representation of sediment deposition and/or the representation of diagenesis may be used to estimate stratigraphy, heterogeneity, reservoir quality, reservoir connectivity, and/or other features in the geographic volume of interest. In some implementations, stratigraphy may be a structure defining an order and relative position of rock layers, and their relationship to a geological time scale.

In some implementations, the stratigraphy may include a carbonate stratigraphy. Carbonate may be a class of sedimentary rock whose primary mineral constituent is a carbonate species (e.g., calcite, aragonite, dolomite, limestone, and/or other carbonate species). Carbonate may be formed through precipitation (e.g., chemical precipitation from seawater) and/or organism activities (e.g., coral, algae, clam shells, and/or other organisms).

In some implementations, server(s) 102, client computing platform(s) 104, and/or external resources 114 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 114 may be operatively linked via some other communication media.

A given client computing platform 104 may include one or more processors configured to execute computer program components. The computer program components may be configured to enable a user corresponding to the given client computing platform 104 to interface with system 100 and/or external resources 114, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 114 may include sources of information outside of system 100, external entities participating with system 100, and/or other resources. In some implementations, some or all of the functionality attributed herein to external resources 114 may be provided by resources included in system 100.

Server(s) 102 may include electronic storage 116, one or more processors 118, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 116 may comprise non-transitory storage media that electronically stores information. The electronic storage media of electronic storage 116 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 116 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 116 may include one or more virtual storage resources (e.g., cloud storage, a virtual private network, and/or other virtual storage resources). Electronic storage 116 may store software algorithms, information determined by processor(s) 118, information received from server(s) 102, information received from client computing platform(s) 104, and/or other information that enables server(s) 102 to function as described herein.

Processor(s) 118 may be configured to provide information processing capabilities in server(s) 102. As such, processor(s) 118 may include one or more of a digital processor, an analog processor, a physical computer processor, a digital circuit designed to process information, an analog circuit designed to process information, a state machine, and/or other mechanisms for electronically processing information. Although processor(s) 118 is shown in FIG. 1 as a single entity, this is for illustrative purposes only. In some implementations, processor(s) 118 may include a plurality of processing units. These processing units may be physically located within the same device, or processor(s) 118 may constitute processing functionality of a plurality of devices operating in coordination. Processor(s) 118 may be configured to execute components 108, 110, 112, and/or other components. Processor(s) 118 may be configured to execute components 108, 110, 112, and/or other components by software; hardware; firmware; some combination of software, hardware, and/or firmware; and/or other mechanisms for configuring processing capabilities on processor(s) 118. As used herein, the term "component" may refer to any individual component or set of components that perform the functionality attributed to the component. This may include one or more physical processors during execution of processor readable instructions, the processor readable instructions, circuitry, hardware, storage media, or any other components.

It should be appreciated that although components 108, 110, and/or 112, are illustrated in FIG. 1 as being implemented within a single processing unit, in implementations in which processor(s) 118 includes multiple processing units, one or more of components 108, 110, and/or 112, may be implemented remotely from the other components. The description of the functionality provided by the different components 108, 110, and/or 112, described below is for illustrative purposes, and is not intended to be limiting, as any of components 108, 110, and/or 112, may provide more or less functionality than is described. For example, one or more of components 108, 110, and/or 112, may be eliminated, and some or all of its functionality may be provided by other ones of components 108, 110, and/or 112. Processor(s) 118 may be configured to execute one or more additional components that may perform some or all of the functionality attributed below to one of components 108, 110, and/or 112.

Figure 2:
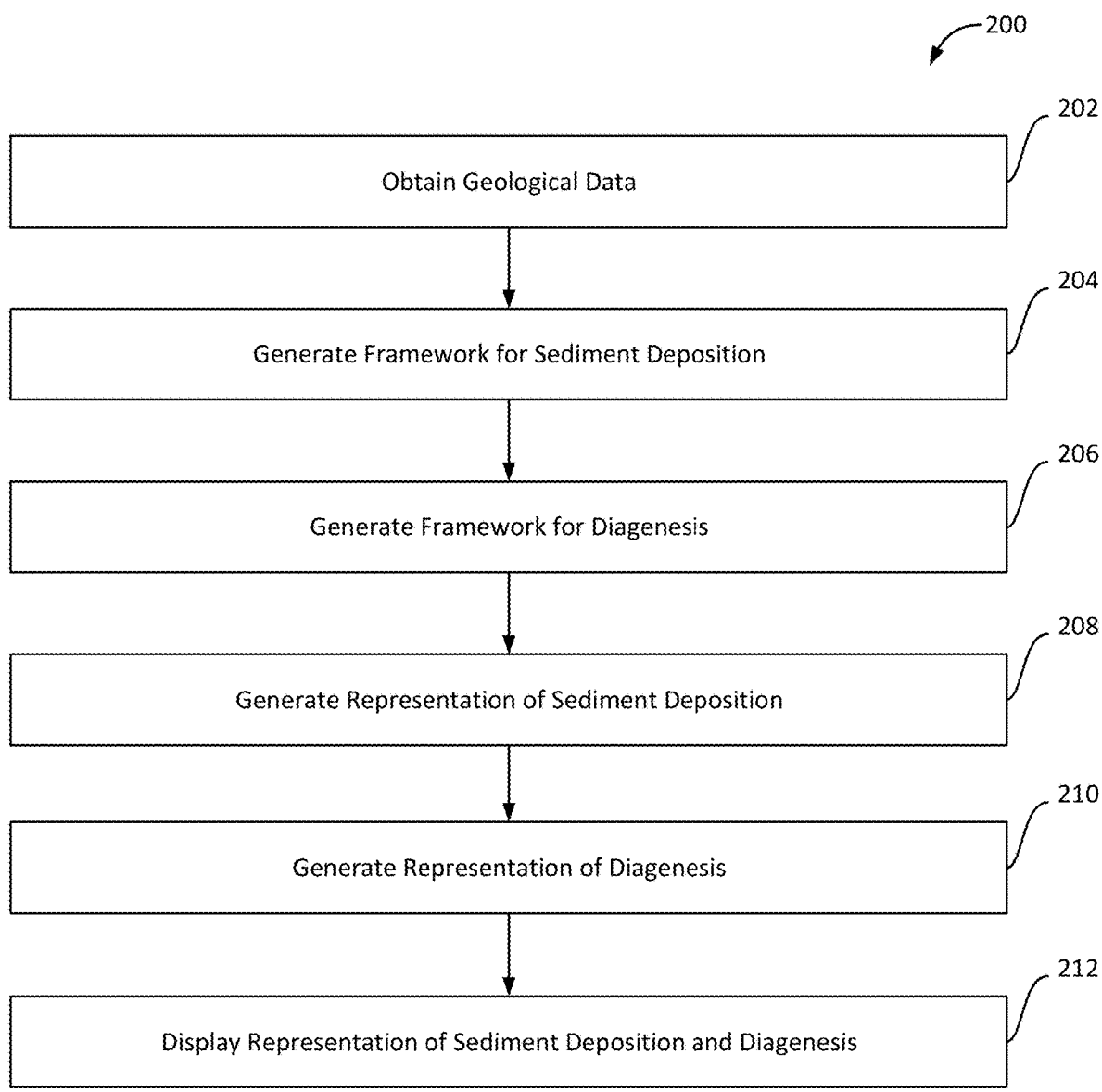
FIG. 2 is a flow chart of a method for estimating reservoir stratigraphy, quality, and connectivity, in accordance with one or more implementations.

FIG. 2 illustrates a method 200 for estimating reservoir stratigraphy, quality, and connectivity, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a physical computer processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include obtaining, from the electronic storage, geological data corresponding to the geographic volume of interest. Operation 202 may be performed by one or more physical computer processors configured by machine-readable instructions including a component that is the same as or similar to data component 108, in accordance with one or more implementations.

An operation 204 may include generating a framework for sediment deposition using a first set of multiple physical, chemical, biological, and geological processes. Operation 204 may be performed by one or more physical computer processors configured by machine-readable instructions including a component that is the same as or similar to framework component 110, in accordance with one or more implementations.

An operation 206 may include generating a framework for diagenesis using a second set of multiple physical, chemical, biological, and geological processes. Operation 206 may be performed by one or more physical computer processors configured by machine-readable instructions including a component that is the same as or similar to framework component 110, in accordance with one or more implementations.

An operation 208 may include generating a representation of sediment deposition by applying the geological data corresponding to the geographic volume of interest to the framework for sediment deposition. The representation of sediment deposition may indicate a change to an amount of sediment in the geographic volume of interest as a function of position and time. Operation 208 may be performed by one or more physical computer processors configured by machine-readable instructions including a component that is the same as or similar to representation component 112, in accordance with one or more implementations.

An operation 210 may include generating a representation of diagenesis based on the framework for diagenesis and the representation of sediment deposition. The representation of diagenesis may indicate a change in porosity and permeability as a function of position and time. Operation 210 may be performed by one or more physical computer processors configured by machine-readable instructions including a component that is the same as or similar to representation component 112, in accordance with one or more implementations.

An operation 212 may include displaying the representation of sediment deposition and the representation of diagenesis on a graphical user interface. Operation 212 may be performed by one or more physical computer processors configured by machine-readable instructions including a component that is the same as or similar to representation component 112, in accordance with one or more implementations.

Figure 3:
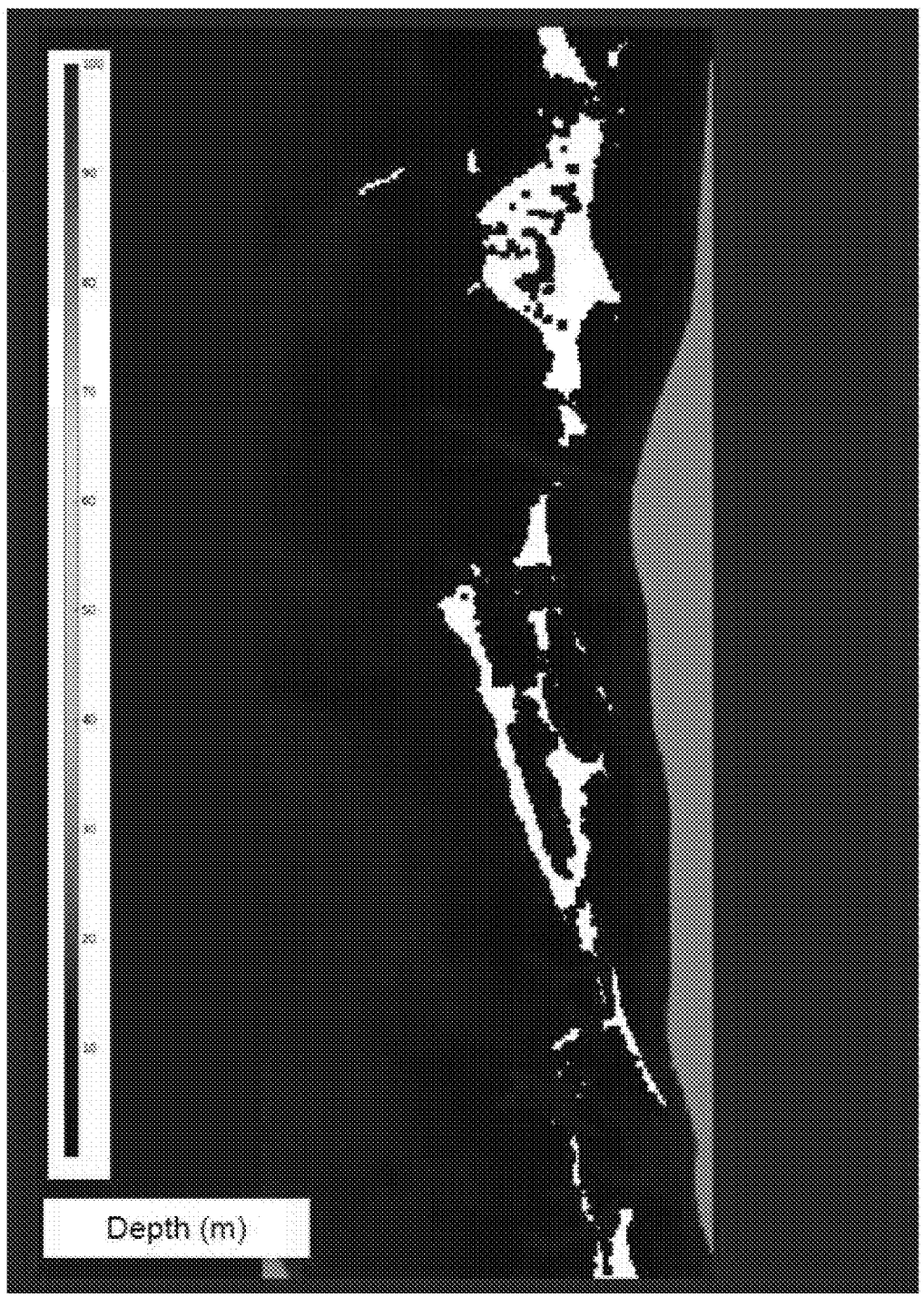
FIG. 3 illustrates water depth within a geographic volume of interest, in accordance with one or more implementations.

FIG. 3 illustrates water depth within a geographic volume of interest, in accordance with one or more implementations. As illustrated, the depth of the ocean increases further away from the bodies of land. The depth of the water illustrates geological data that may be used to generate a framework for sediment deposition and the framework for diagenesis.

Figure 4B:
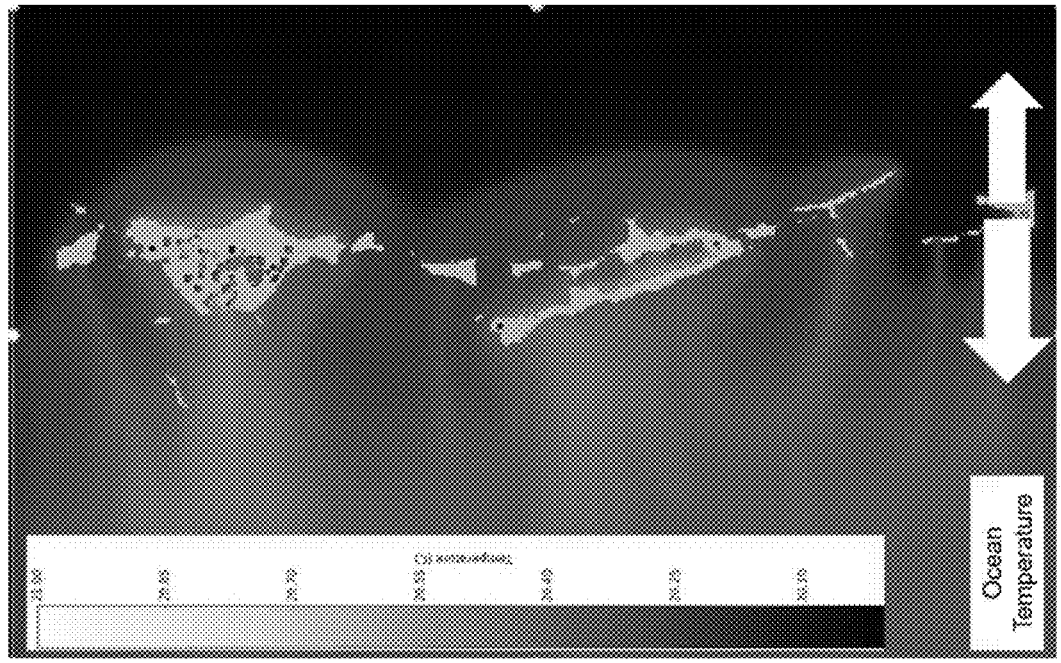
FIG. 4B illustrates ocean temperature at a second time within a geographic volume of interest, in accordance with one or more implementations.
Figure 4A:
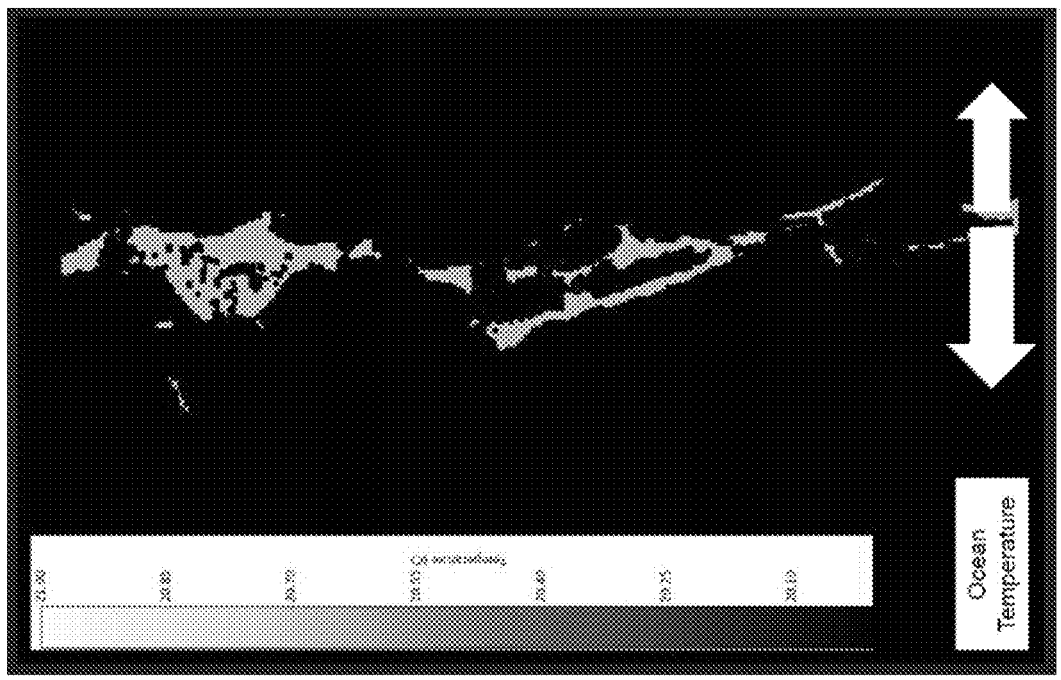
FIG. 4A illustrates ocean temperature at a first time within a geographic volume of interest, in accordance with one or more implementations.
Figure 4D:
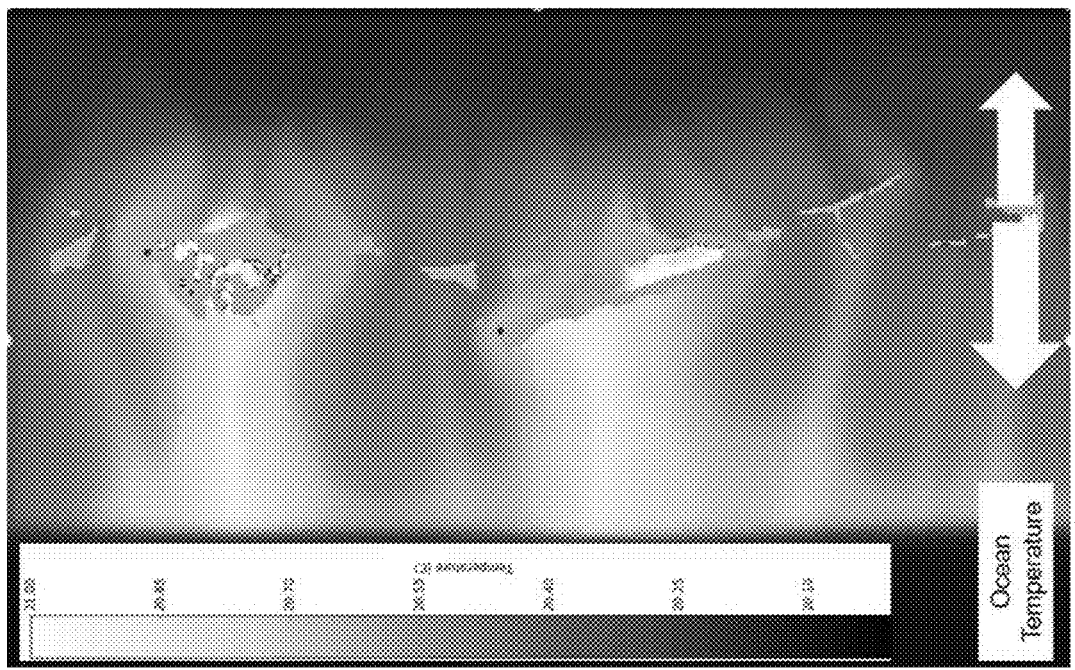
FIG. 4D illustrates ocean temperature at a fourth time within a geographic volume of interest, in accordance with one or more implementations.
Figure 4C:
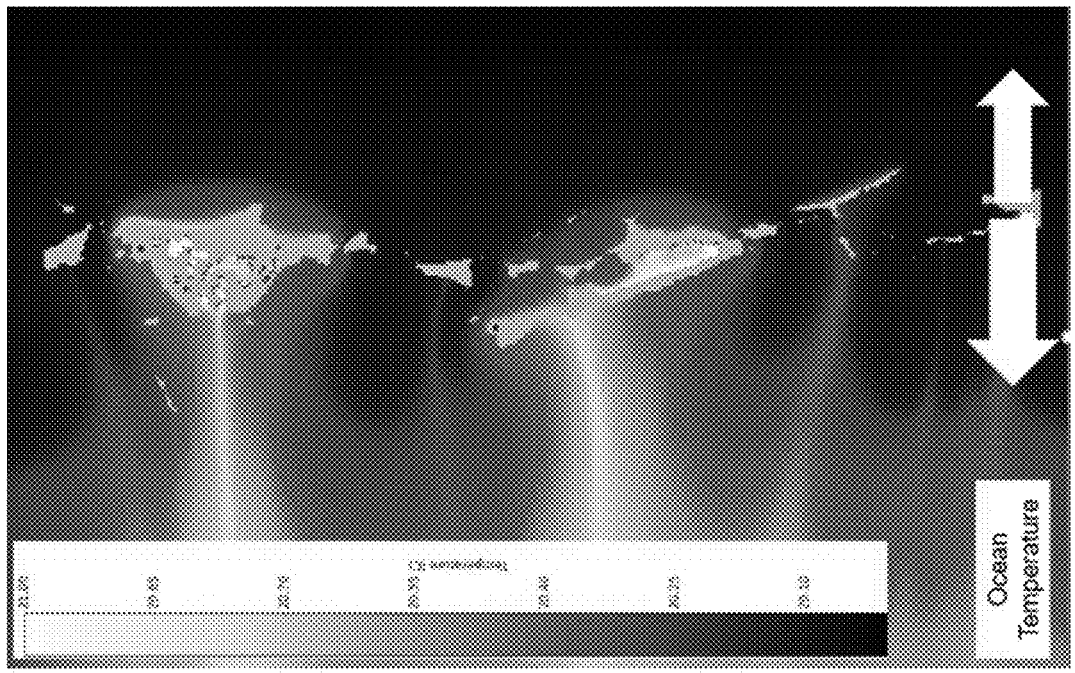
FIG. 4C illustrates ocean temperature at a third time within a geographic volume of interest, in accordance with one or more implementations.

FIGS. 4A-4D illustrates ocean temperature within a geographic volume of interest over a period of time, in accordance with one or more implementations. At least FIGS. 4-6, 12, and 13 may illustrate an area of about twelve kilometers to about five kilometers at a resolution of about twenty-five meters with an asymmetrical twelve hour tide with a fifty centimeter magnitude. FIG. 4A may illustrate a first time, where a representation of the change in ocean temperature around bodies of land is beginning. FIG. 4B may illustrate a second time, where the tide has been moving right to left, affecting ocean temperature, such that the left side of the bodies of land is warmer than the right side of the bodies of land. FIG. 4C may illustrate a third time, after the tide has gone through several cycles, where the ocean temperature is warmest along the left side of certain areas extending from the bodies of land. FIG. 4D may illustrate a fourth time, where the ocean temperature is warmest along the left side of the bodies of land as the tide pushes from left to right. It should be appreciated that the first time, the second time, the third time and so on, as used herein, may not be separated by the same time intervals.

Figures 5A, 5B:
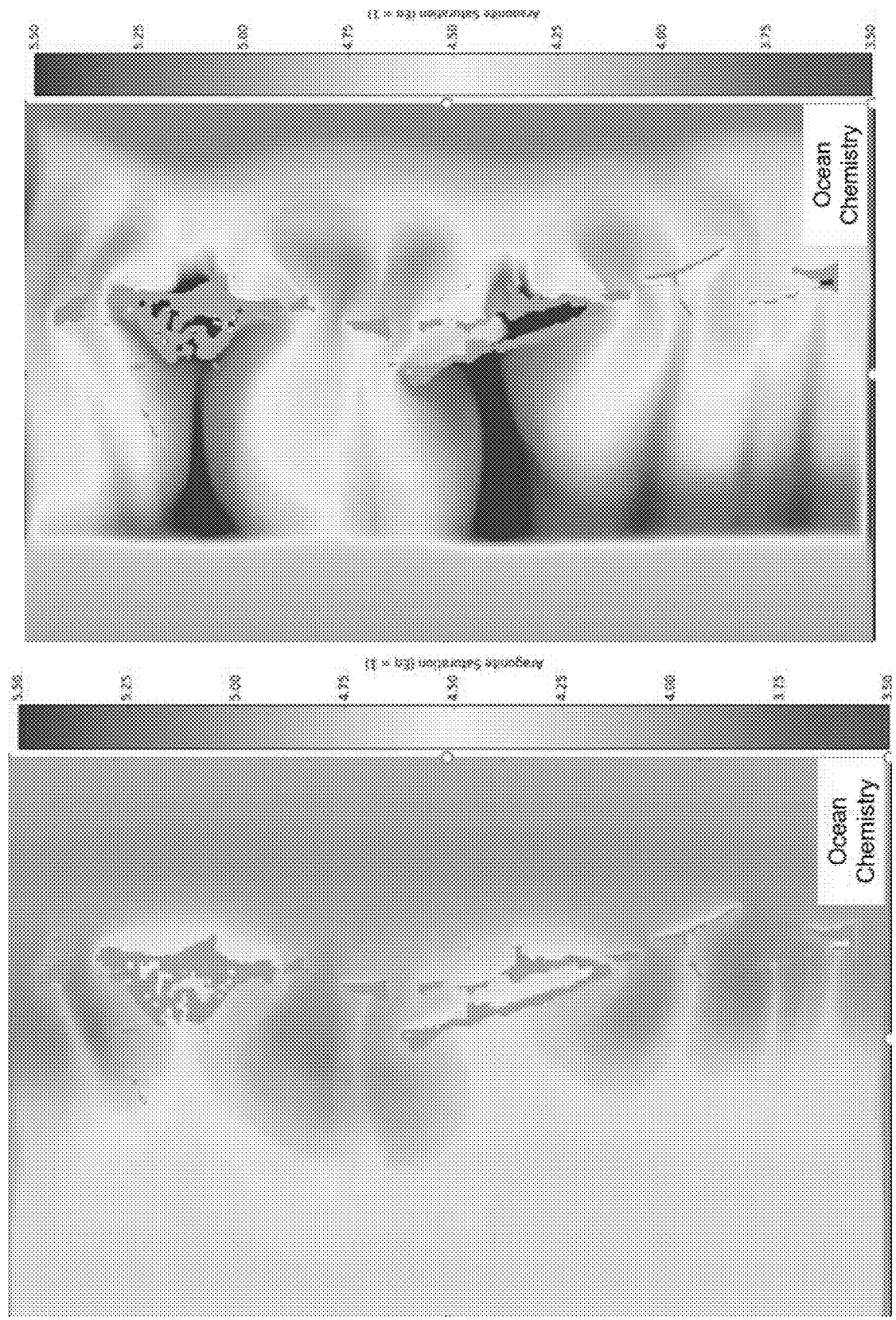
FIG. 5A illustrates ocean chemistry at a first time within a geographic volume of interest, in accordance with one or more implementations.
FIG. 5B illustrates ocean chemistry at a second time within a geographic volume of interest, in accordance with one or more implementations.
Figure 5D:
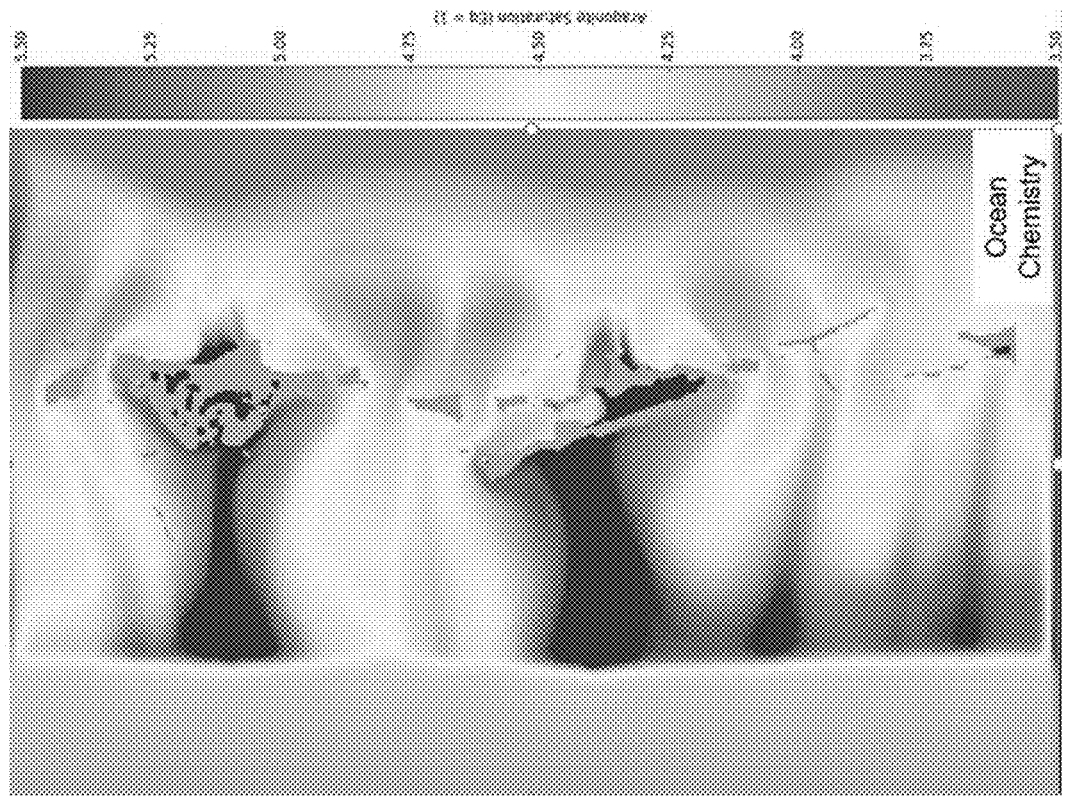
FIG. 5D illustrates ocean chemistry at a fourth time within a geographic volume of interest, in accordance with one or more implementations.
Figure 5C:
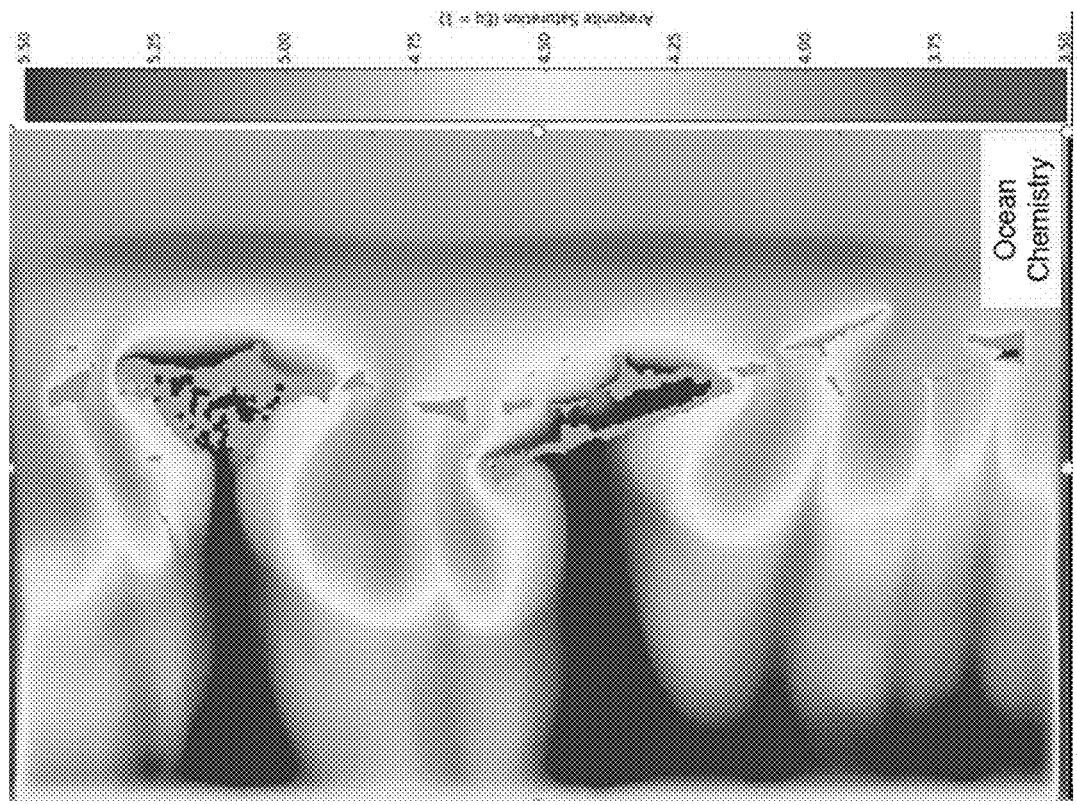
FIG. 5C illustrates ocean chemistry at a third time within a geographic volume of interest, in accordance with one or more implementations.

FIGS. 5A-5D illustrates ocean chemistry (specifically, the chemical saturation of ocean water with respect to the calcium carbonate mineral, aragonite) within a geographic volume of interest, in accordance with one or more implementations. As illustrated, ocean chemistry is affected by the chemical saturation of ocean water with respect to the calcium carbonate mineral, aragonite. In implementations, the aragonite saturation varies as a function of changing temperature, $CO_2$ content in the water, and changes in salinity. The aragonite saturation is closer to equilibrium on the right of the bodies of land and further from equilibrium on the left of the bodies of land. Aragonite saturation may be defined by the equation:

$$\Omega_{aragonite} = \frac{[Ca^{2+}] \times [CO_3^{2-}]}{K_{sp_{aragonite}}}$$

where $K_{sp_{aragonite}}$ is the solubility product constant for aragonite, which is temperature and salinity dependent. The ocean chemistry (including Ca, CO$_3$, pH, salinity, and/or other chemical components) illustrates geological data that may be used to generate a framework for sediment deposition and the framework for diagenesis. Referring to FIG. 5A, this may illustrate an initial aragonite saturation at a first time. FIG. 5B may illustrate the aragonite saturation at a second time, as the tide has been moving from left to right. Aragonite saturation is highest to the left of the aragonite saturation, which corresponds in part to the ocean temperature. At FIG. 5C, the tide is moving from right to left and aragonite saturation is highest around the bodies of land and to the left of the bodies of land at a third time. The lowest aragonite saturation is on the right side of the bodies of land. Finally, in FIG. 5D, as in FIG. 5C, the aragonite saturation is highest around the bodies of land and to the left of the bodies of land at a fourth time.

Figure 6B:
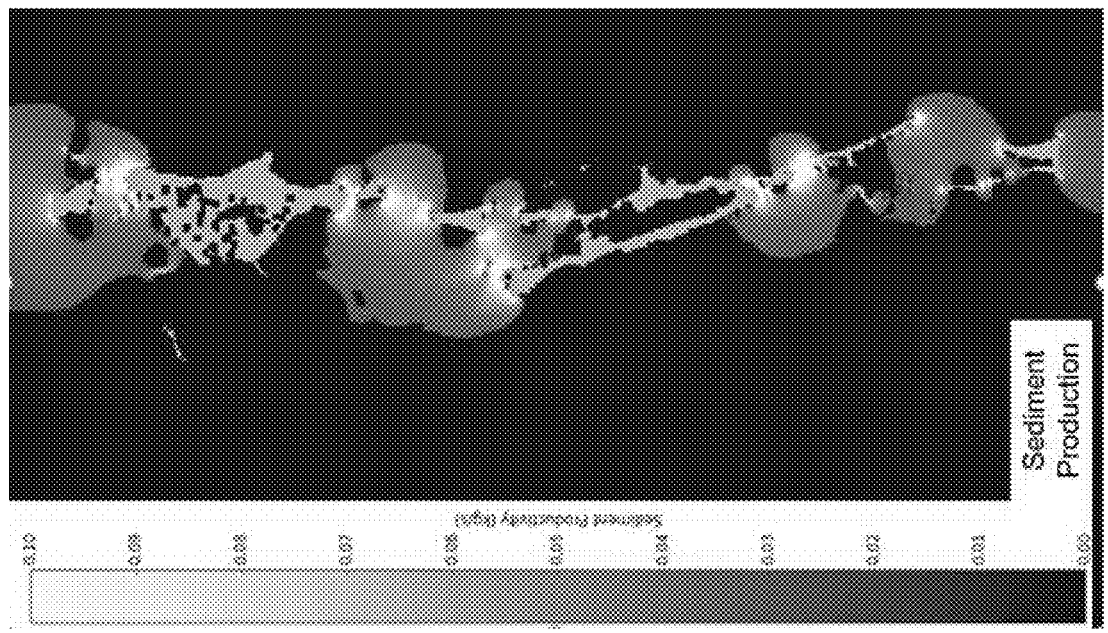
FIG. 6B illustrates sediment production within a geographic volume of interest at a second time, in accordance with one or more implementations.
Figure 6A:
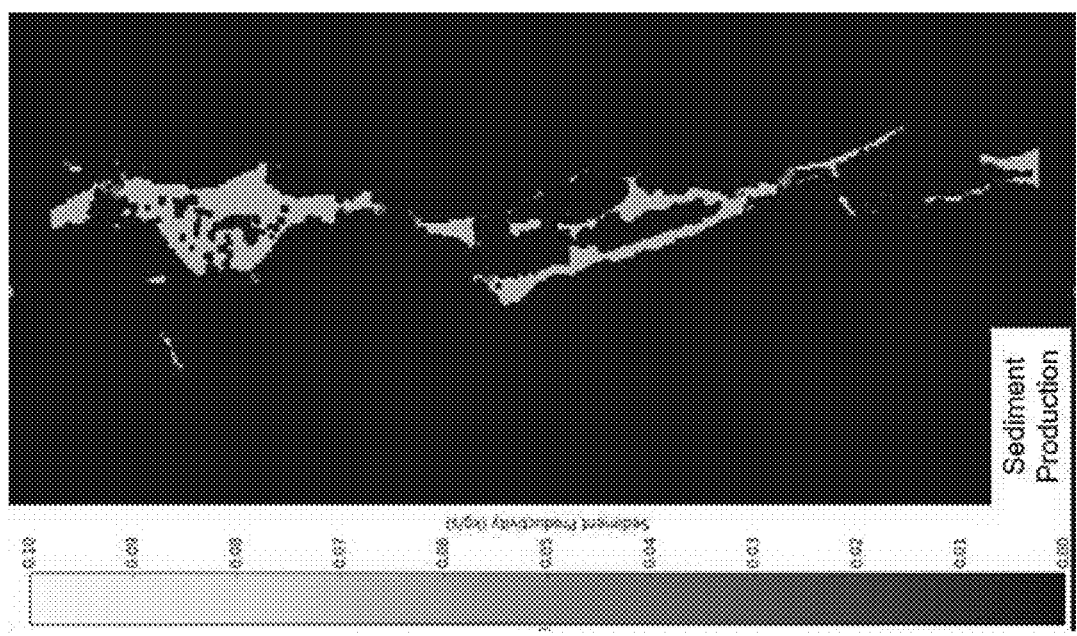
FIG. 6A illustrates sediment production within a geographic volume of interest at a first time, in accordance with one or more implementations.

FIGS. 6A and 6B illustrates sediment production within a geographic volume of interest, in accordance with one or more implementations. Referring to FIG. 6A, an initial sediment productivity at a first time is illustrated. The most productivity occurs around the bodies of land. FIG. 6B illustrates sediment productivity at a second time, as the tide has been moving across the bodies of land. Sediment productivity is greatest around the bodies of land, particularly in channels between bodies of land. The sediment production illustrates geological data that may be used to generate a framework for sediment deposition.

Figure 7:
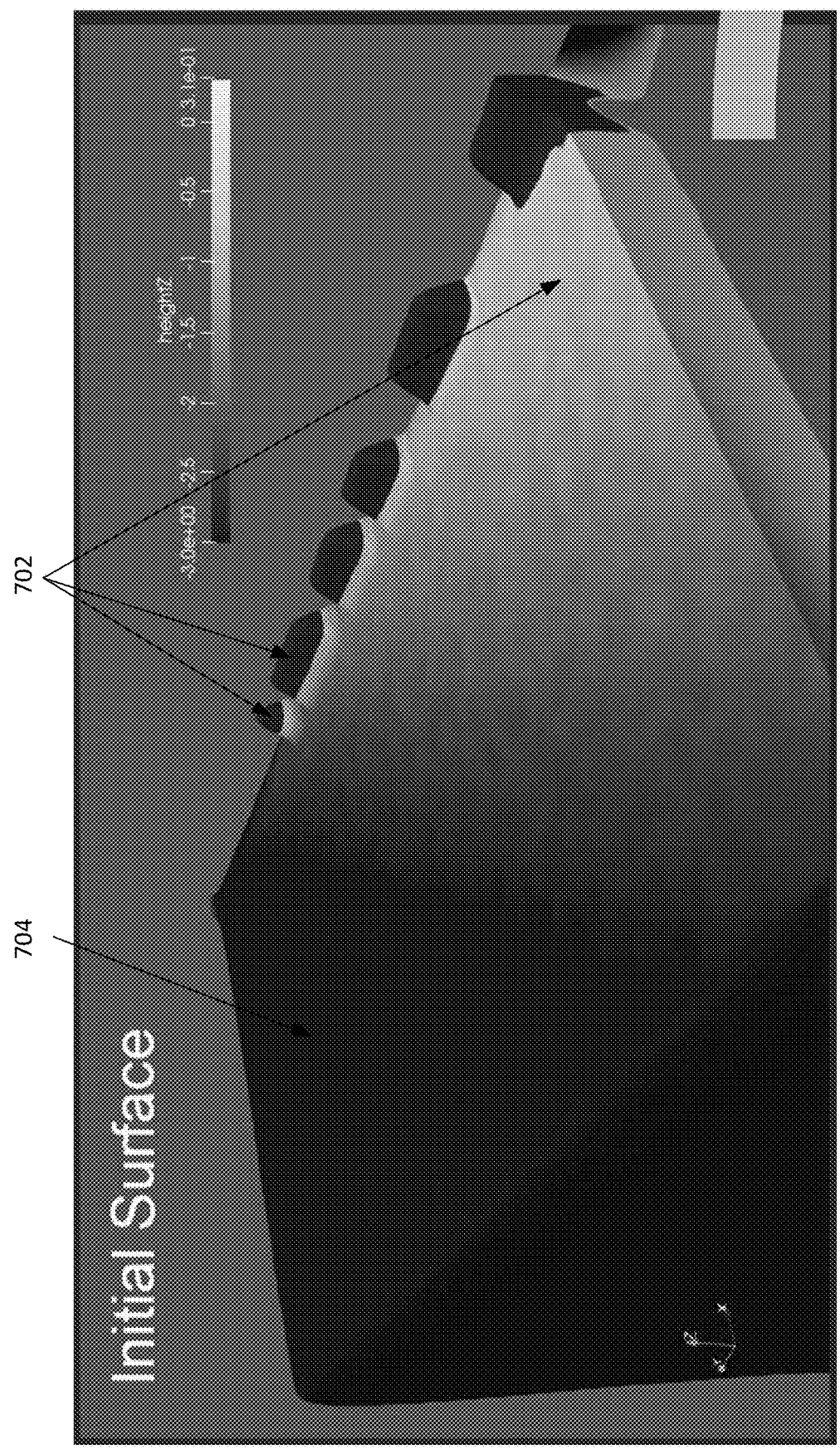
FIG. 7 illustrates an example representation of sediment deposition, in accordance with one or more implementations.

FIG. 7 illustrates an example representation of sediment deposition, in accordance with one or more implementations. As illustrated, the representation of sediment deposition may correspond to a first time. The representation of sediment deposition may include bodies of land 702 and body of water 704. The first time may be the start time.

Figure 8:
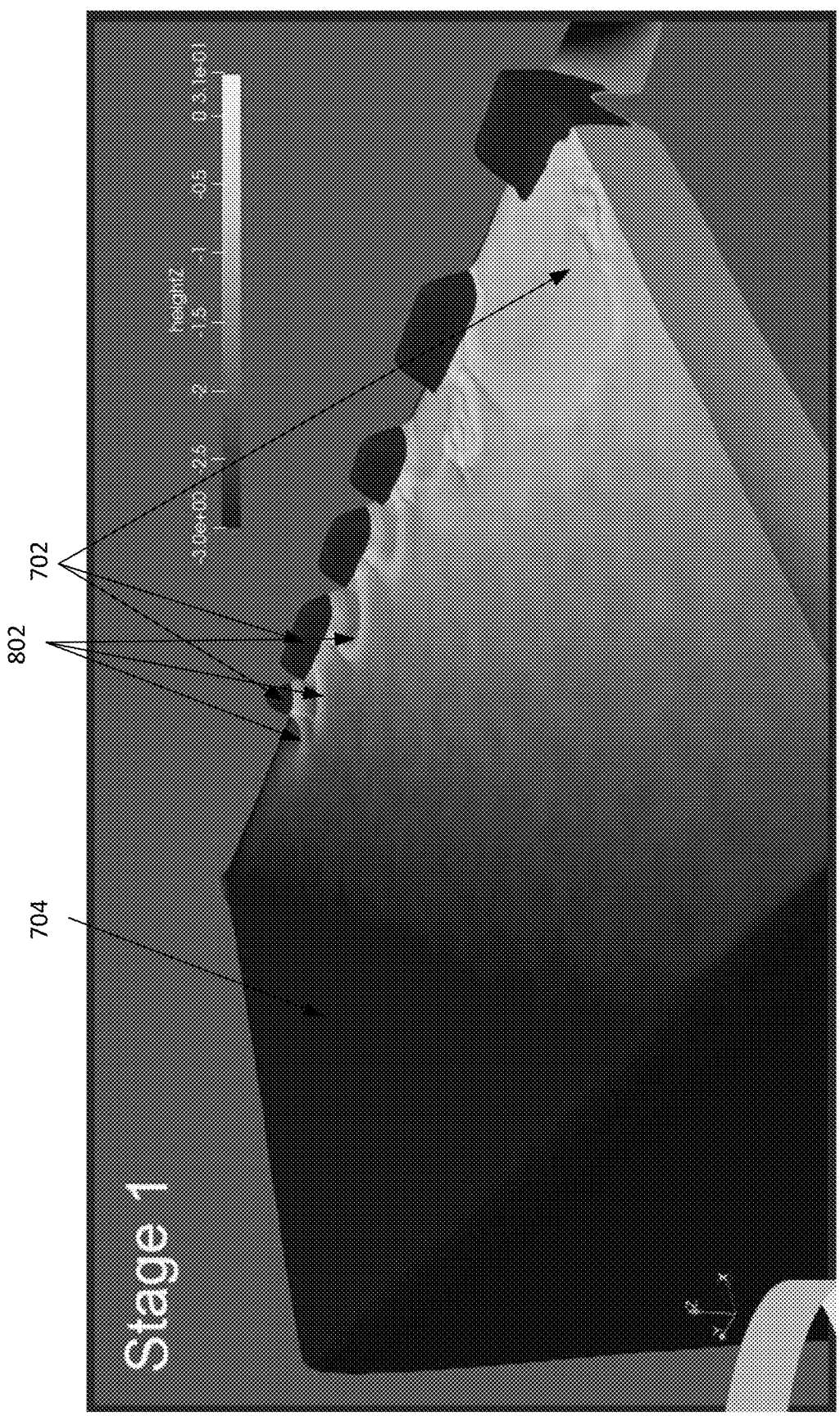
FIG. 8 illustrates an example representation of sediment deposition, in accordance with one or more implementations.

FIG. 8 illustrates an example representation of sediment deposition, in accordance with one or more implementations. As illustrated, the representation of sediment deposition may correspond to a second time. The second time may be after the first time of FIG. 7. The representation of sediment deposition may include bodies of land 702 and body of water 704, as described above. Sediment bodies 802 may start to form underneath the ocean surface as a result of sediment precipitation and deposition.

Figure 9:
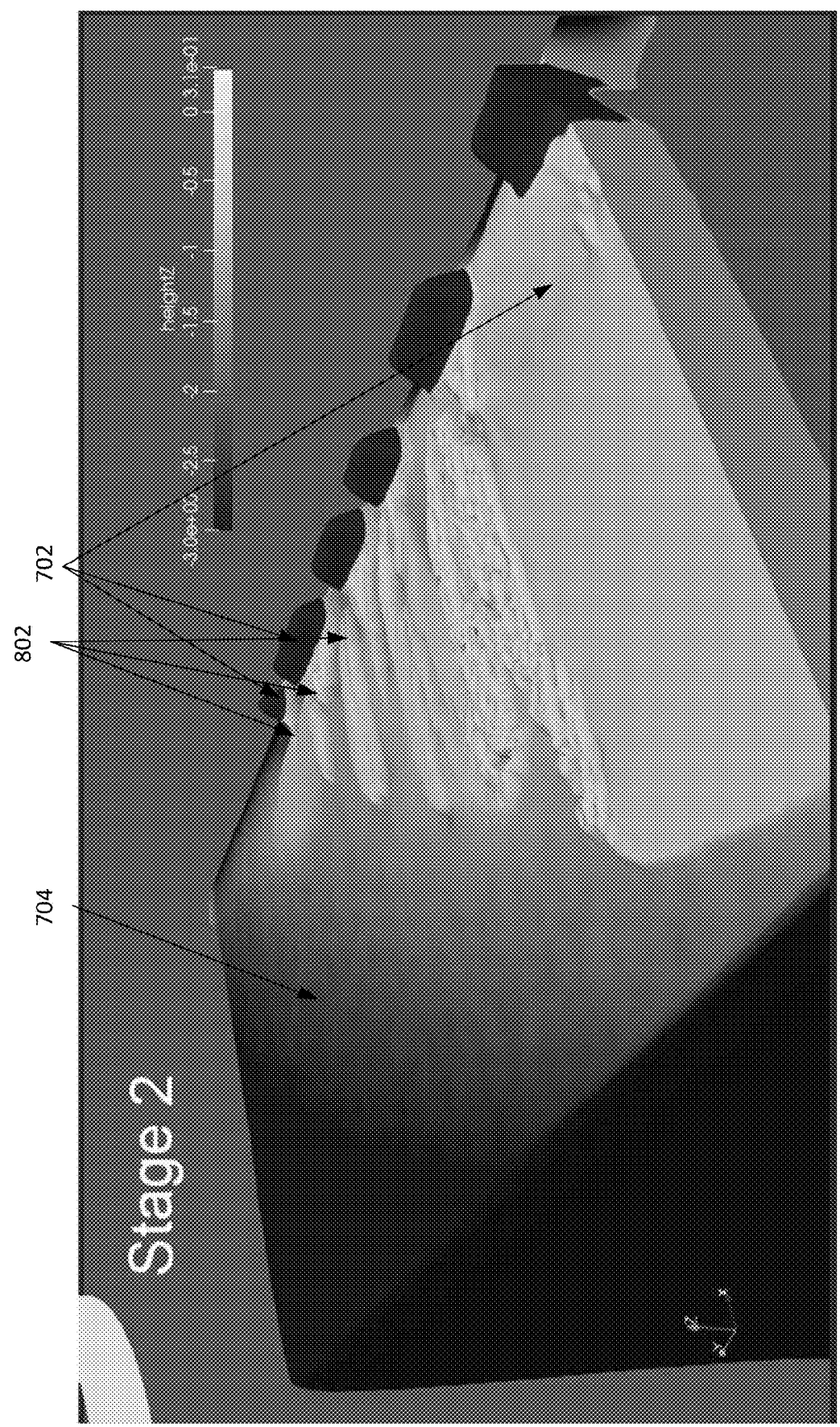
FIG. 9 illustrates an example representation of sediment deposition, in accordance with one or more implementations.

FIG. 9 illustrates an example representation of sediment deposition, in accordance with one or more implementations. As illustrated, the representation of sediment deposition may correspond to a third time. The third time may be after the second time of FIG. 8. The representation of sediment deposition may include bodies of land 702 and body of water 704, as described above. Sediment 802 may be more fully formed underneath the ocean surface as a result of precipitation and deposition.

Figure 10:
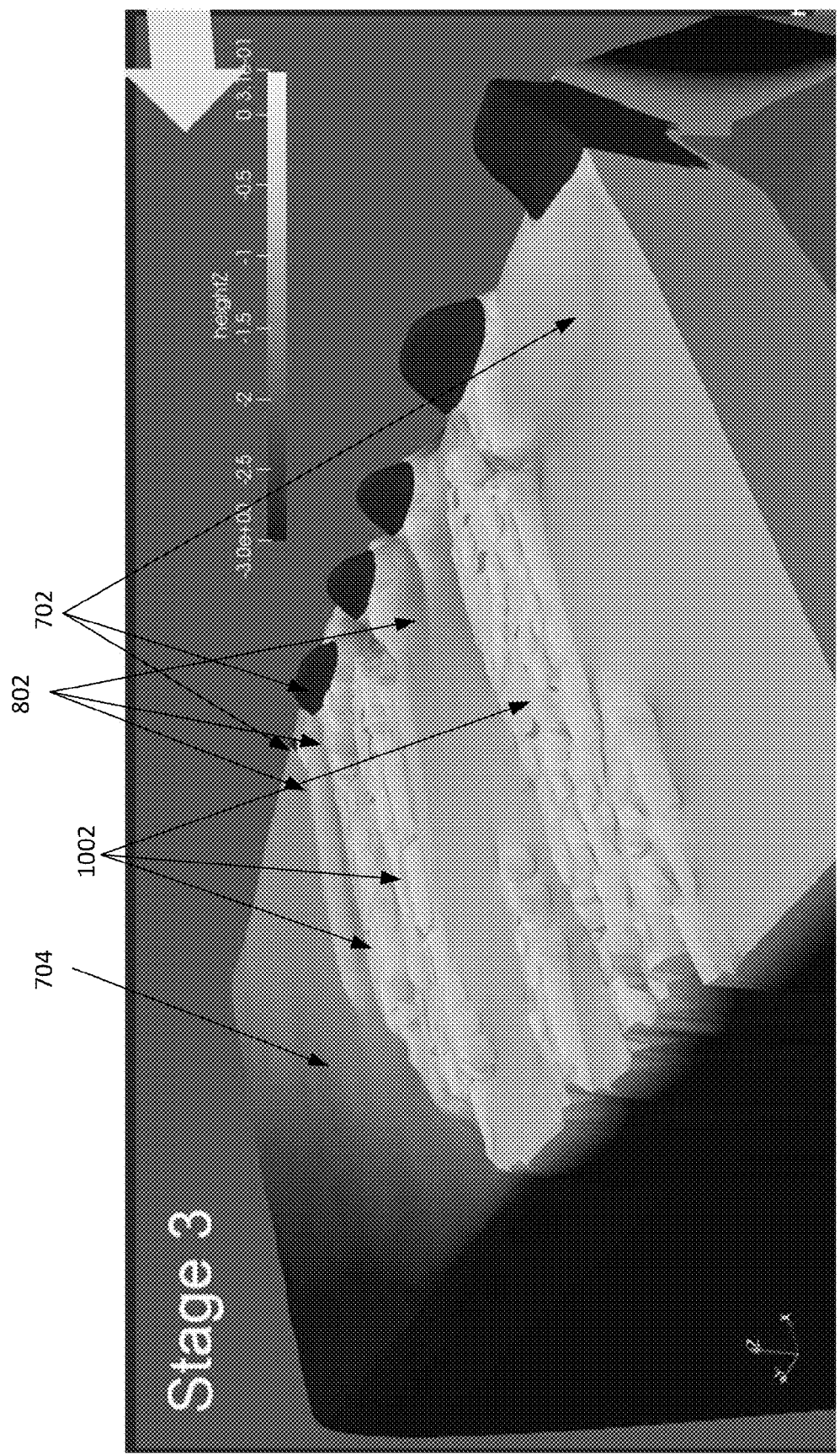
FIG. 10 illustrates an example representation of sediment deposition, in accordance with one or more implementations.

FIG. 10 illustrates an example representation of sediment deposition, in accordance with one or more implementations. As illustrated, the representation of sediment deposition may correspond to a fourth time. The fourth time may be after the third time of FIG. 9. The representation of sediment deposition may include bodies of land 702 and body of water 704, as described above. Sediment 802 may be more fully formed underneath the ocean surface. Islands 1002 may pass the ocean surface as a result of continued sediment precipitation and deposition. Diagenesis may have started in the representation of sediment deposition.

Figure 11:
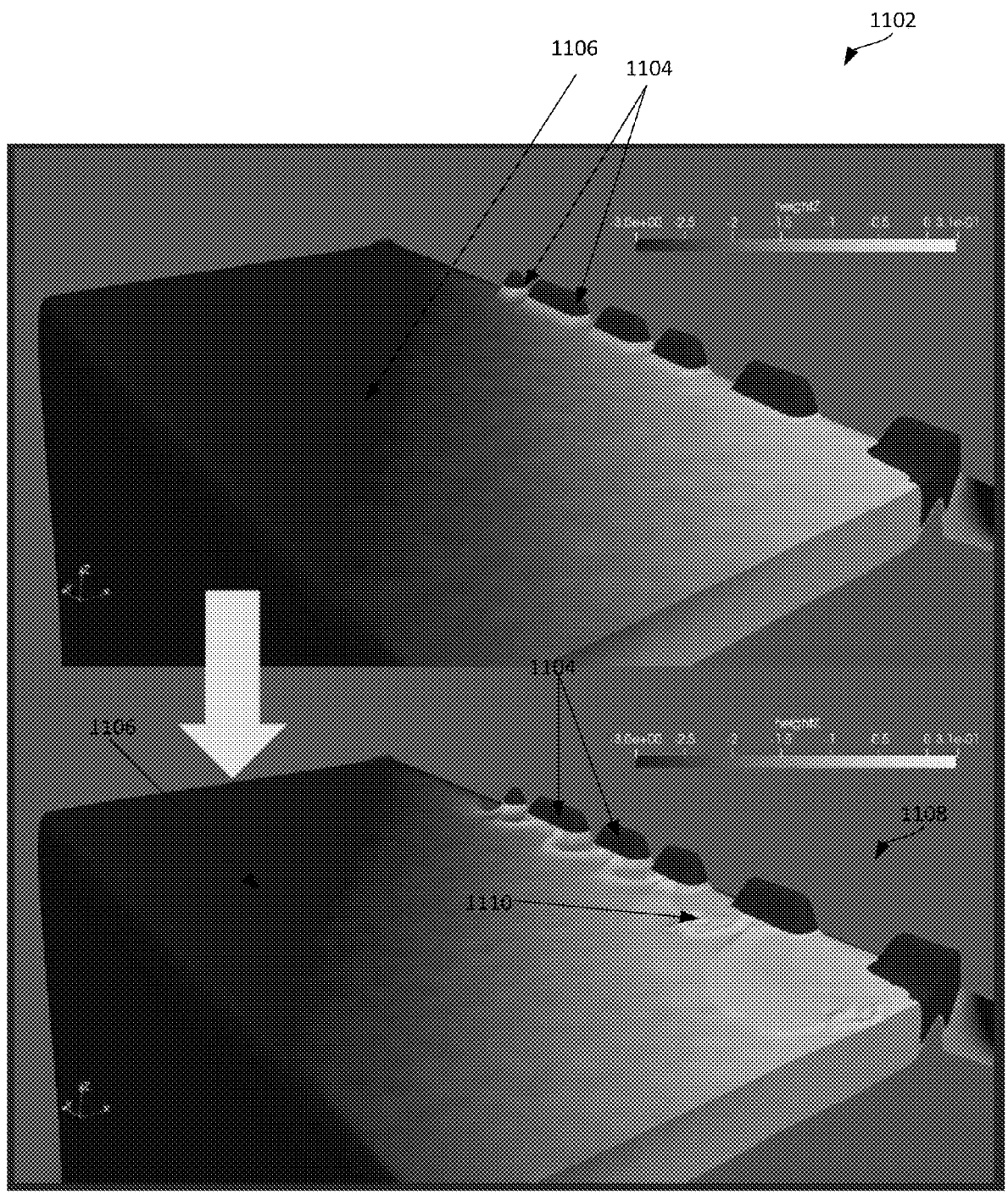
FIG. 11 illustrates changes to example representation of sediment depositions, in accordance with one or more implementations.

FIG. 11 illustrates changes to example representation of sediment depositions, in accordance with one or more implementations. As illustrated, representation of sediment deposition 1102 may correspond to a first time. The representation of sediment deposition may include bodies of land 1104 and body of water 1106. The first time may be the start time. As illustrated, representation of sediment deposition 1108 may correspond to a second time. The second time may be after the first time. Representation of sediment deposition 1108 may include bodies of land 1104 and body of water 1106, as described above. Channelized sediment bodies 1110 may start to form underneath the ocean surface as a result of sediment precipitation and deposition.

Figure 12B:
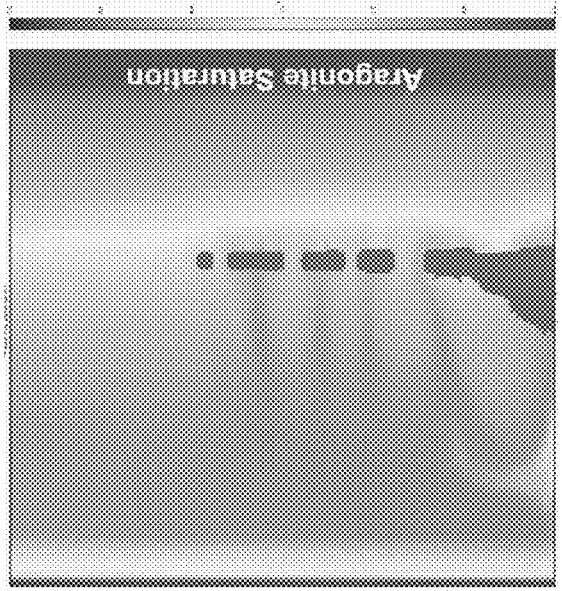
FIG. 12B illustrates the saturation state of seawater with respect to aragonite in a geographic volume of interest at a second time, in accordance with one or more implementations.
Figure 12C:
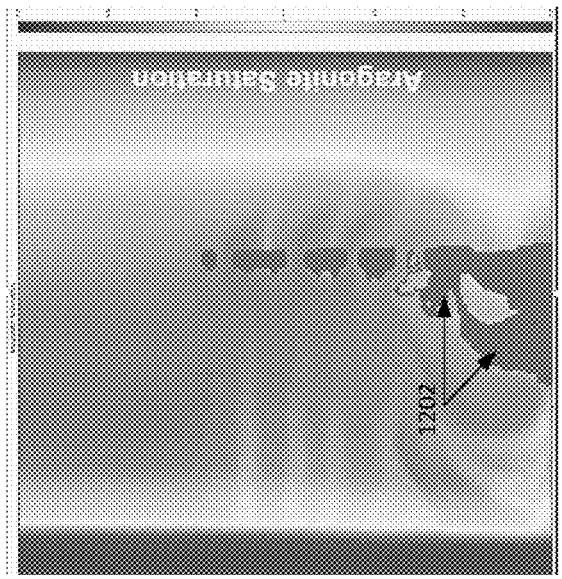
FIG. 12C illustrates the saturation state of seawater with respect to aragonite in a geographic volume of interest at a third time, in accordance with one or more implementations.
Figure 12A:
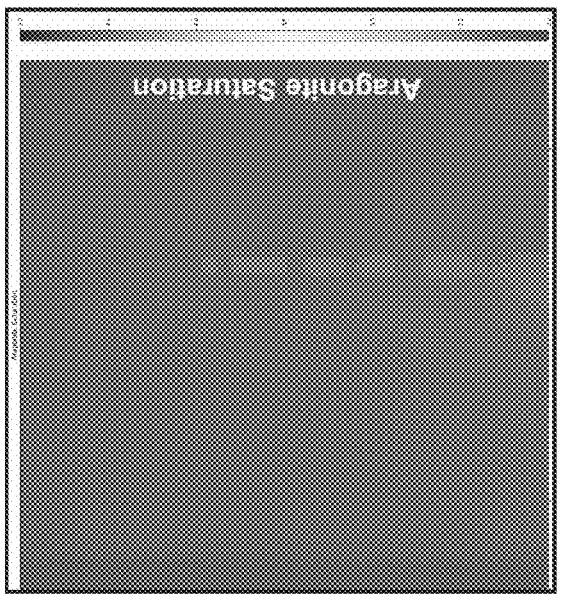
FIG. 12A illustrates the saturation state of seawater with respect to aragonite in a geographic volume of interest at a first time, in accordance with one or more implementations.
Figure 12E:
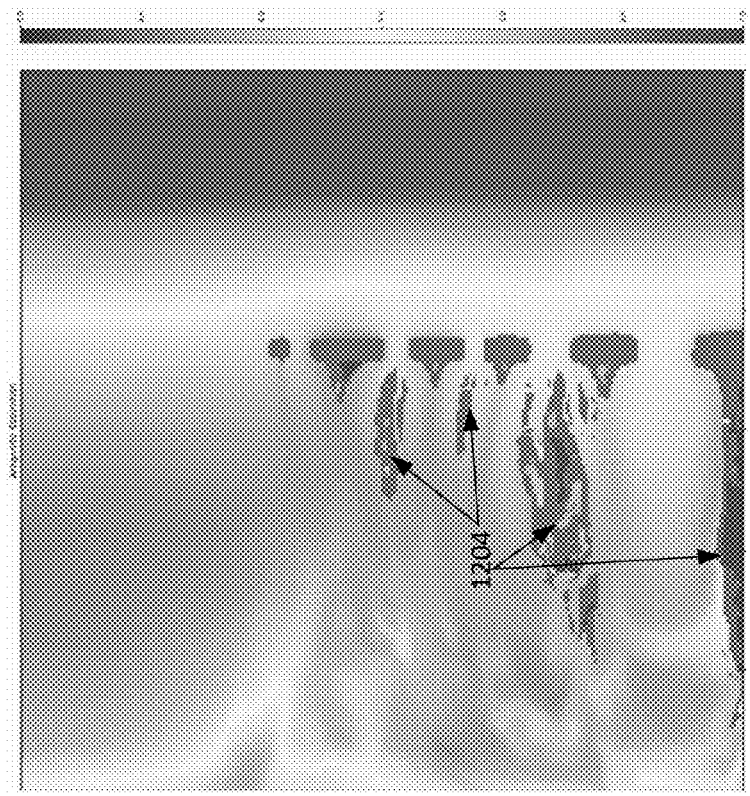
FIG. 12E illustrates the saturation state of seawater with respect to aragonite in a geographic volume of interest at a fifth time, in accordance with one or more implementations.
Figure 12D:
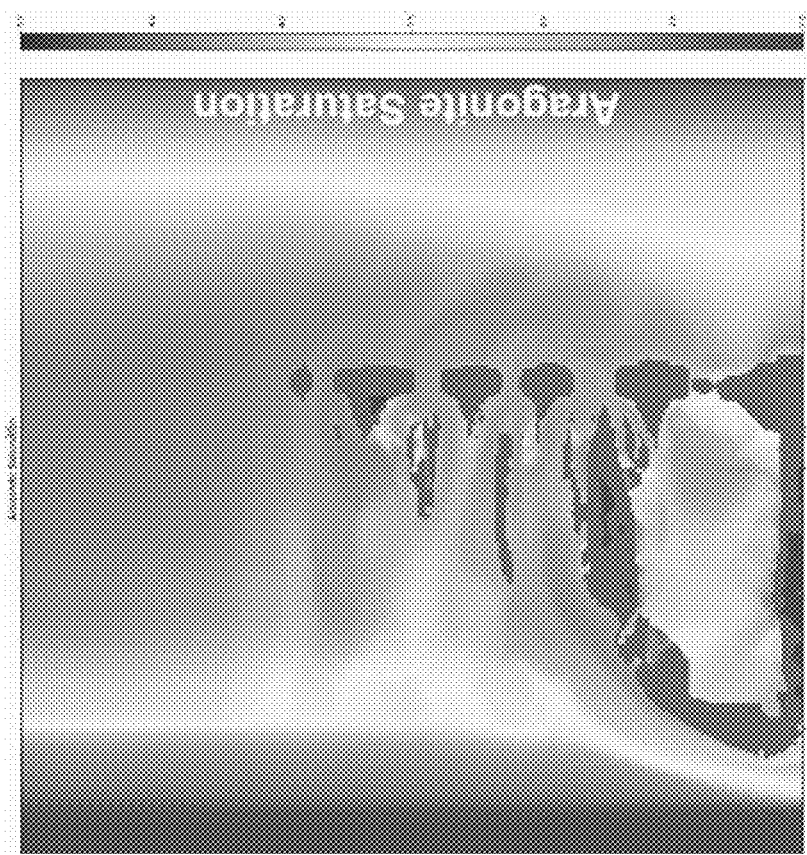
FIG. 12D illustrates the saturation state of seawater with respect to aragonite in a geographic volume of interest at a fourth time, in accordance with one or more implementations.

FIGS. 12A-E illustrates a saturation state of seawater with respect to aragonite in a geographic volume of interest, in accordance with one or more implementations. Referring to FIG. 12A, initial aragonite saturation at a first time is illustrated. In FIG. 12B, aragonite saturation is illustrated at a second time as the tide moves from right to left and the saturation state of the seawater is highest to the left of the bodies of land. In FIG. 12C, unstabilized sand flats 1202 develop at a third time, as the tide moves from right to left to left to right. In FIG. 12D, at a fourth time, the unstabilized sand flats partially disappear as the tide moves the sediment back to the left. In FIG. 12E, additional bodies of land 1204 develop as sediment is deposited over multiple tide cycles at a fifth time. The aragonite saturation illustrates geological data that may be used to generate a framework for sediment deposition and the framework for diagenesis.

Figure 13B:
FIG. 13B illustrates oolitic sediment production in a geographic volume of interest at a second time, in accordance with one or more implementations.
Figure 13A:
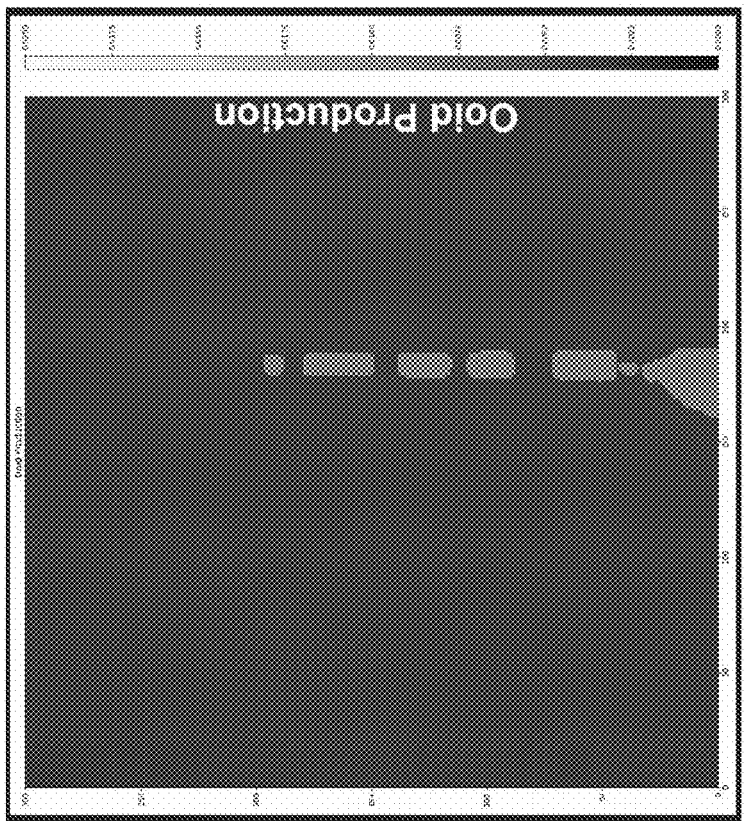
FIG. 13A illustrates oolitic sediment production in a geographic volume of interest at a first time, in accordance with one or more implementations.
Figure 13D:
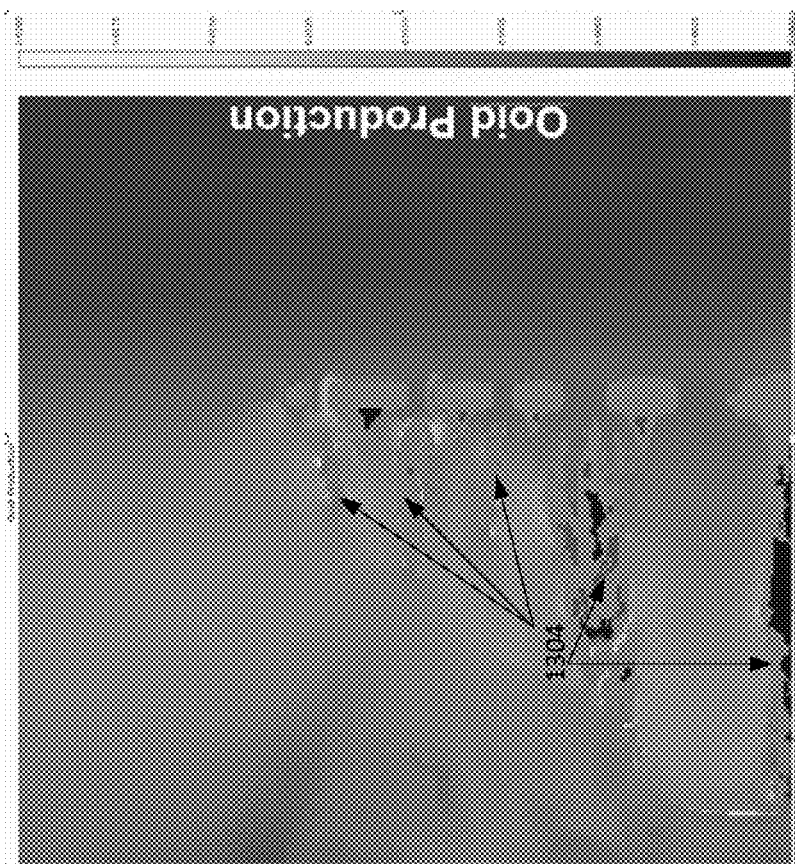
FIG. 13D illustrates oolitic sediment production in a geographic volume of interest at a fourth time, in accordance with one or more implementations.
Figure 13C:
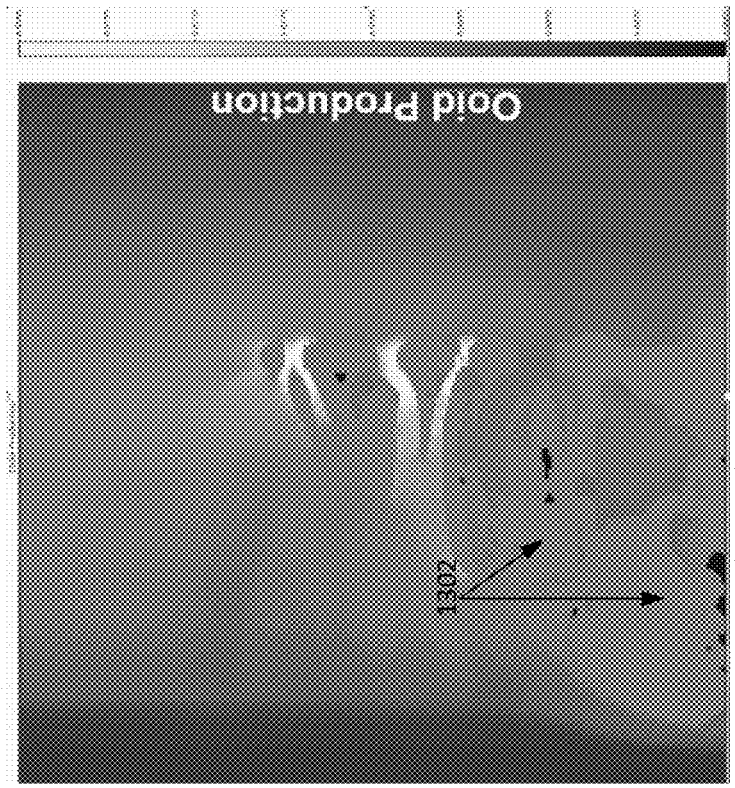
FIG. 13C illustrates oolitic sediment production in a geographic volume of interest at a third time, in accordance with one or more implementations.

FIG. 13A-D illustrates ooid production in a geographic volume of interest, in accordance with one or more implementations. FIG. 13A illustrates initial ooid production at a first time, which is at the very bottom of the scale for the area surrounding the bodies of land. In FIG. 13B, at a second time, as the tide moves through the bodies of land, unstabilized sand flats 1302 develop. Ooid production is highest between the bodies of land and adjacent on the left side of the bodies of land. In FIG. 13C, at a third time, sediment may have deposited forming additional bodies of land 1304. Unstabilized sand flats 1302 may have grown in size, and ooid production is highest between the bodies of land and to the left of the bodies of land as the tide moves through the bodies of land. In FIG. 13D at a fourth time, the additional bodies of land 1304 are more pronounced as the unstabilized sand flats 1302 have been washed away by the tide. The ooid production represents geological data that may be used to generate a framework for sediment deposition and the framework for diagenesis.

Figure 14:
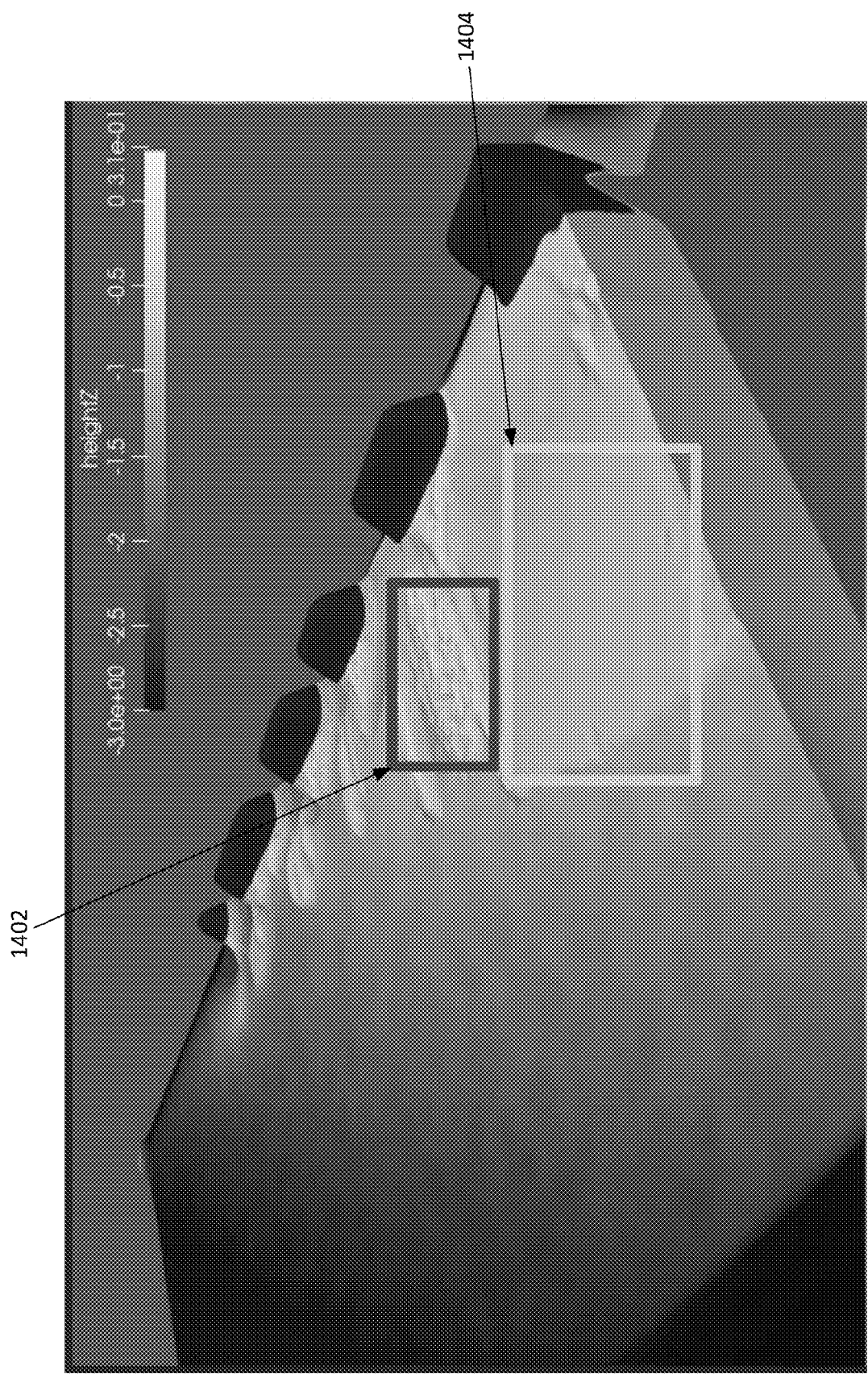
FIG. 14 illustrates channelized sand flats forming in an example representation of sediment deposition, in accordance with one or more implementations.
Figure 15:
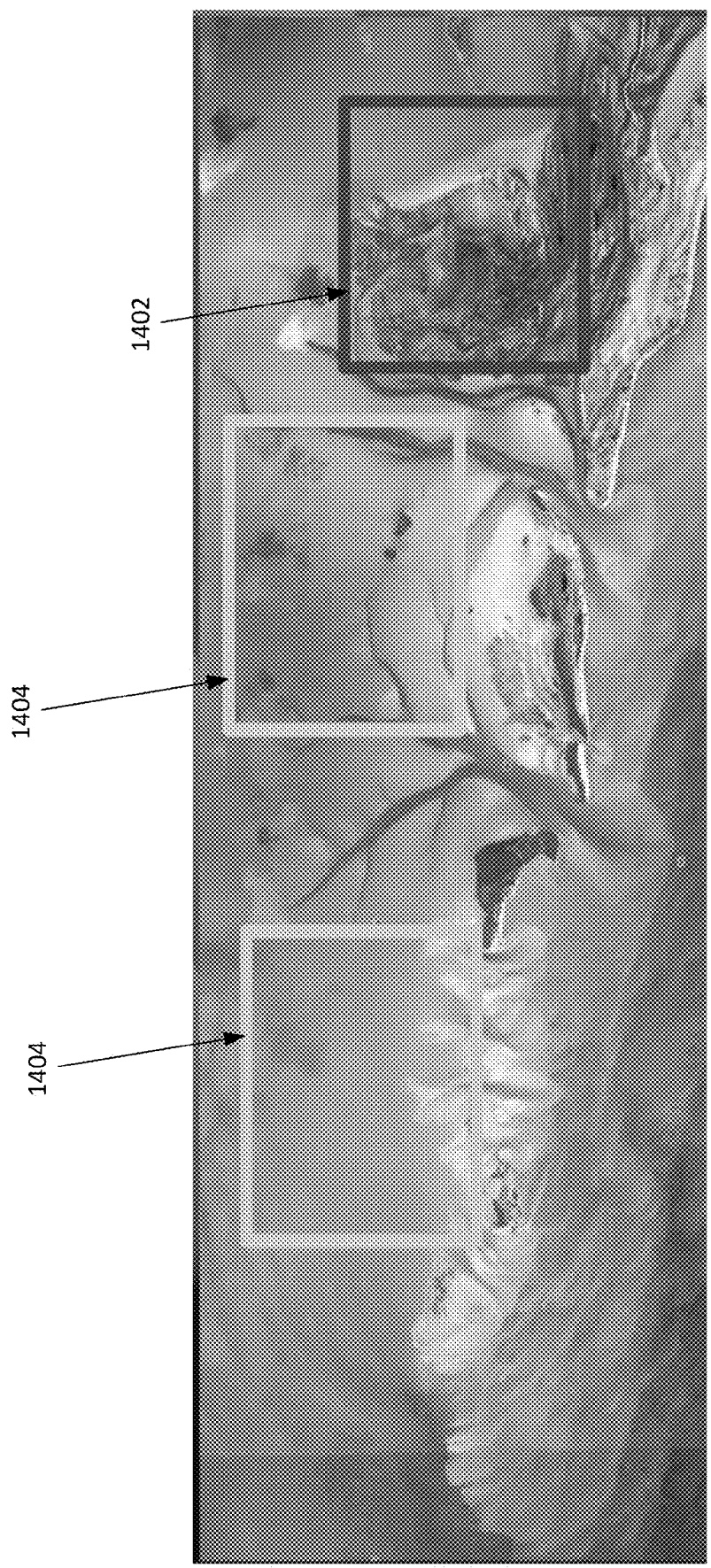
FIG. 15 illustrates satellite images of channelized sand flats forming in a geographic volume of interest.
Figure 16:
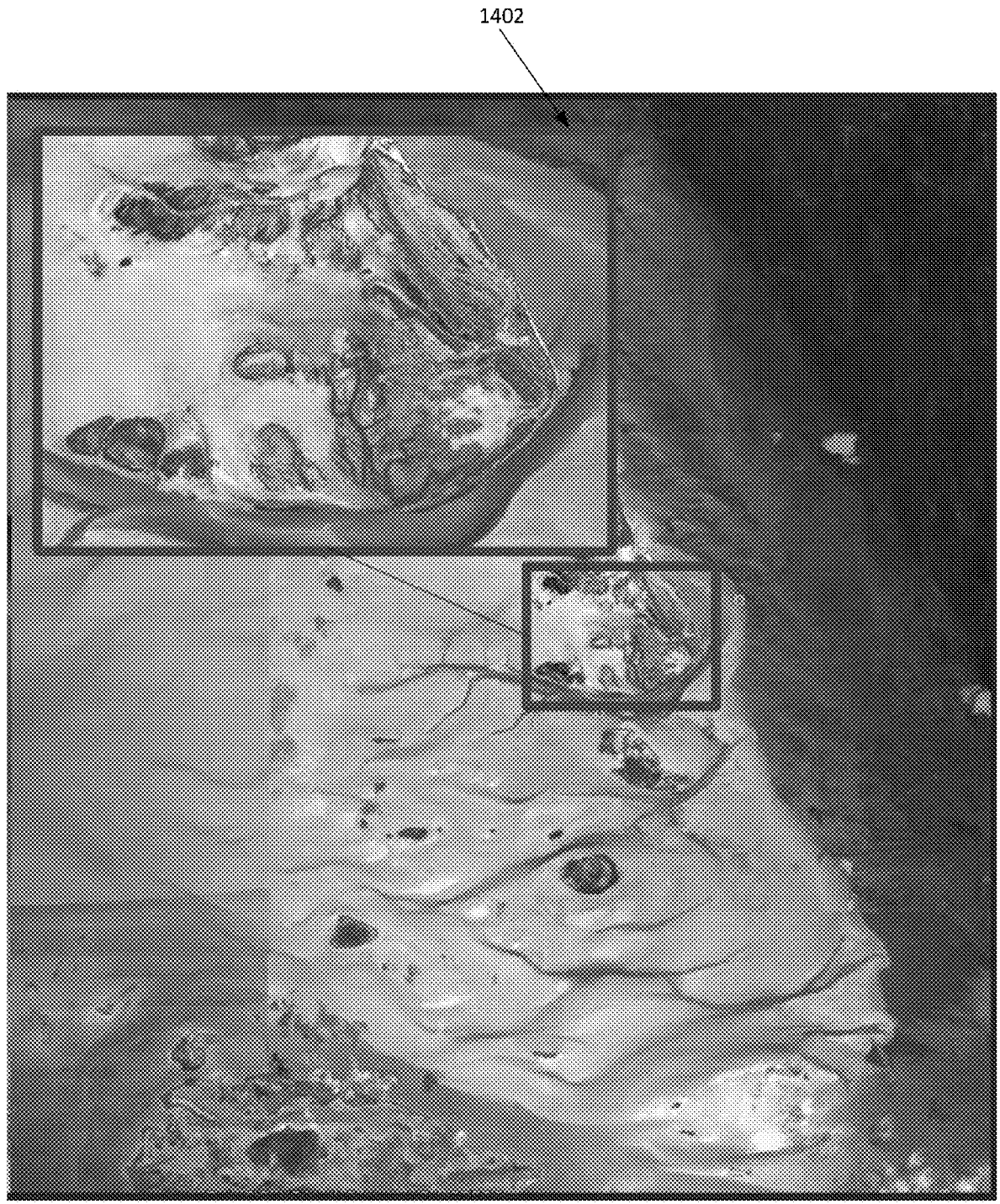
FIG. 16 illustrates satellite images of channelized sand flats forming in a geographic volume of interest.

FIG. 14 illustrates channelized sand flats forming in an example representation of sediment deposition, in accordance with one or more implementations. As illustrated, box 1402 identifies channelized sandflats corresponding to real-world locations, as illustrated in FIGS. 15 and 16. Box 1404 identifies sandflats corresponding to real-world locations, as illustrated in FIGS. 15 and 16.

FIG. 15 illustrates satellite images of channelized sand flats forming in an example representation of sediment deposition, in accordance with one or more implementations. As illustrated, box 1402 identifies channelized sandflats and tidal flats. Box 1404 identifies sandflats.

FIG. 16 illustrates satellite images of channelized sand flats forming in an example representation of sediment deposition, in accordance with one or more implementations. As illustrated, box 1402 identifies a channelized sandflat magnified from a top view of the geographic volume of interest.

Figure 17:
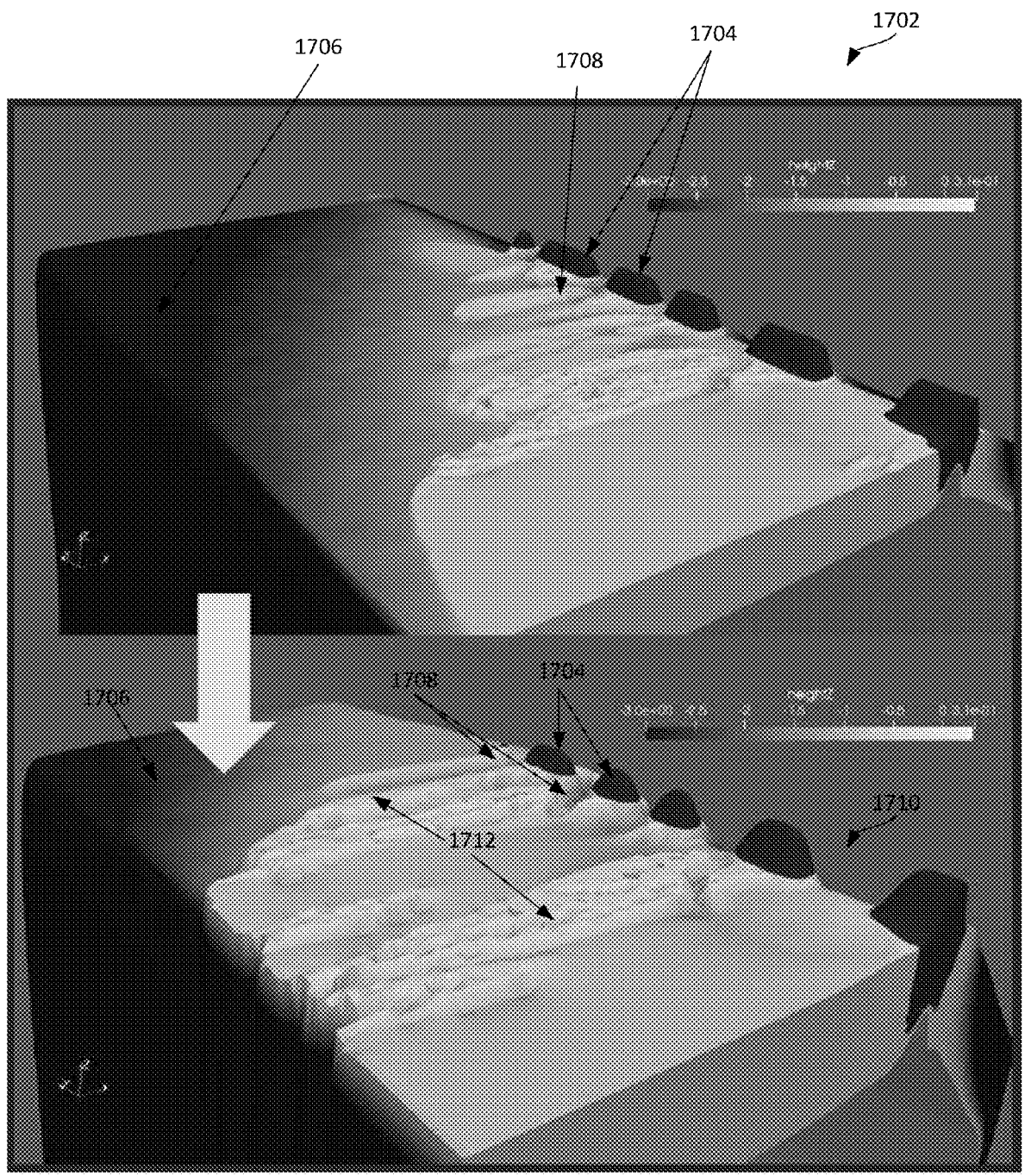
FIG. 17 illustrates changes to example representation of sediment depositions, in accordance with one or more implementations.

FIG. 17 illustrates changes to example representation of sediment depositions, in accordance with one or more implementations. As illustrated, representation of sediment deposition 1702 may correspond to a third time. The third time may be after the second time of FIG. 11. The representation of sediment deposition may include bodies of land 1704 and body of water 1706. Channels 1708 may start to form underneath the ocean surface as a result of sediment precipitation and deposition. As illustrated, representation of sediment deposition 1710 may correspond to a fourth time. The fourth time may be after the third time. Representation of sediment deposition 1708 may include the bodies of land 1704 and the body of water 1706, as described above. Islands 1712 may pass the ocean surface as a result of continued sediment precipitation and deposition. Diagenesis may have started in representation of sediment deposition 1710.

Figure 18:
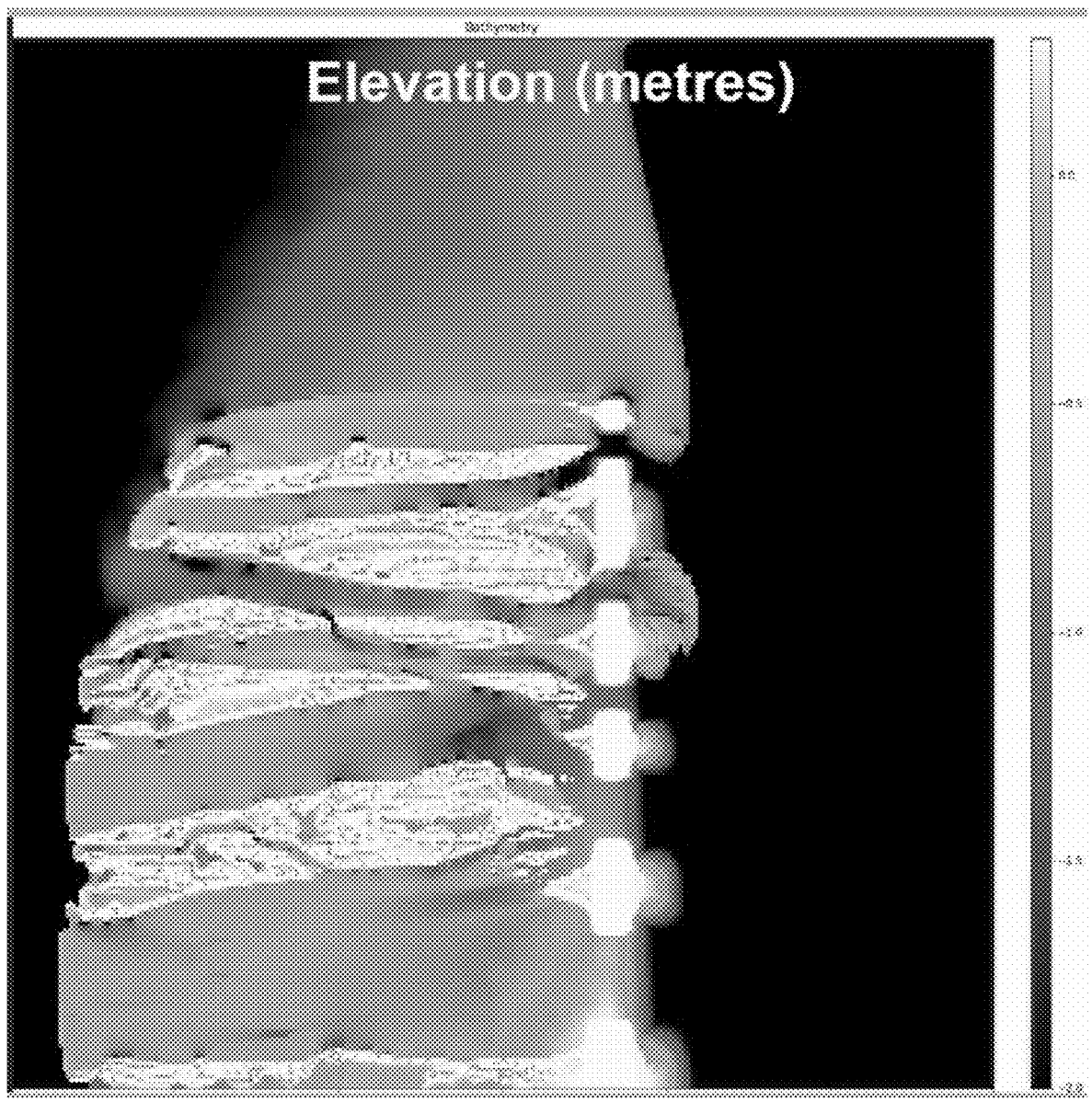
FIG. 18 illustrates elevation of a geographic volume of interest at a single snapshot in time, in accordance with one or more implementations.

FIG. 18 illustrates elevation of a geographic volume of interest, in accordance with one or more implementations. The bathymetry of the geographic volume of interest, or the measurement of depth of water in oceans, seas, lakes, and/or other bodies of water, indicates the sediment deposition is highest in the tail end of shoals and sediment transport is highest within channels. Flow and sediment movement is highest between shoals, where unstabilized sand flats and channels exist.

Figure 19:
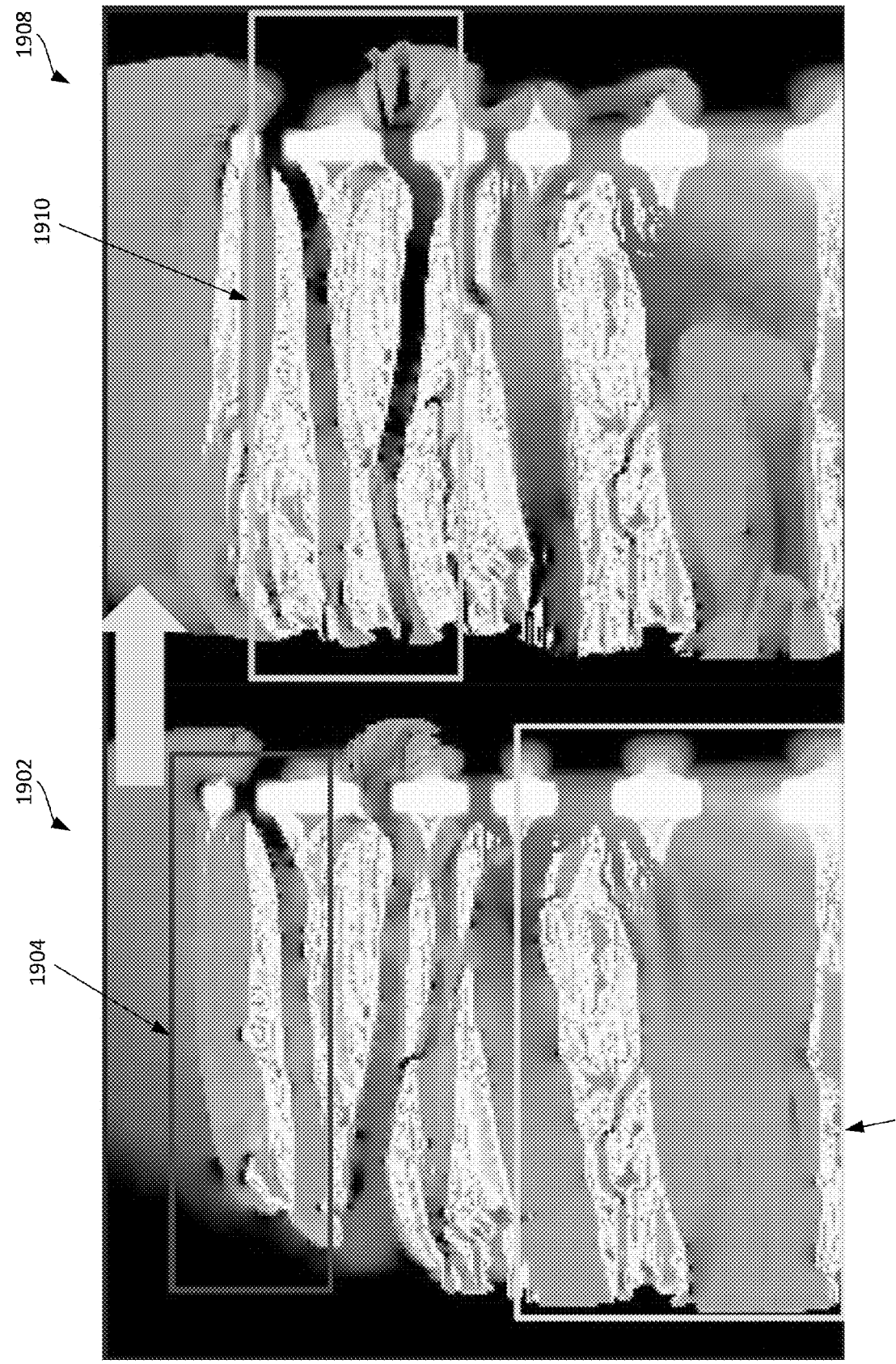
FIG. 19 illustrates changes in elevation of a geographic volume of interest, in accordance with one or more implementations.

FIG. 19 illustrates changes in elevation of a geographic volume of interest, in accordance with one or more implementations. As illustrated, geographic volume of interest 1902 is at a third time and geographic volume of interest 1908 is at a fourth time corresponding to the example representation of sediment depositions of FIG. 17. The amount of sediment deposited increases in geographic volume of interest 1908, resulting in higher levels of sediment around the existing sediment in geographic volume of interest 1902. Box 1904 identifies progradation, or the forward growth of carbonate sediment deposits into the ocean over time. Box 1906 identifies sediment reworking and bay fill. Box 1910 identifies channel incision, or where sand flats are separated from each other based on flow and tide of the ocean.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A computer-implemented method for estimating reservoir stratigraphy, quality, and connectivity in a geographic volume of interest, the method being implemented in a computer system, the computer system including one or more physical computer processors and non-transient electronic storage, the method comprising:
    obtaining, from the electronic storage, geological data corresponding to the geographic volume of interest;
    generating a framework for sediment deposition using a first set of multiple physical, chemical, biological, and geological processes, the first set of multiple physical, chemical, biological, and geological processes determining precipitation of carbonate sediment from seawater;
    generating a representation of sediment deposition by applying the geological data corresponding to the geographic volume of interest to the framework for sediment deposition, wherein the representation of sediment deposition indicates a change to an amount of the carbonate sediment in the geographic volume of interest as a function of position and time due to the precipitation of the carbonate sediment from the seawater, and wherein the representation of sediment deposition indicates a formation of a rock volume resulting from the change to the amount of the carbonate sediment in the geographic volume of interest as the function of position and time, the rock volume including carbonate pore structure; and
    displaying the representation of sediment deposition on a graphical user interface.

2. The computer-implemented method of claim 1, further comprising:
    generating a framework for diagenesis using a second set of multiple physical, chemical, biological, and geological processes, the second set of multiple physical, chemical, biological, and geological processes determining changes to the carbonate pore structure in the rock volume;
    generating a representation of diagenesis based on the framework for diagenesis and the representation of sediment deposition, wherein the representation of diagenesis indicates a change in porosity and permeability as a function of position and time due to the changes in the carbonate pore structure in the rock volume; and
    displaying the representation of diagenesis on the graphical user interface.

3. The computer-implemented method of claim 2, wherein the first set of multiple physical, chemical, biological, and geological processes is different from the second set of multiple physical, chemical, biological, and geological processes.

4. The computer-implemented method of claim 2, wherein the second set of multiple physical, chemical, biological, and geological processes comprises a groundwater circulation representation and a reactive groundwater representation.

5. The computer-implemented method of claim 2, wherein the changes in the carbonate pore structure in the rock volume includes changes in shape, size, and chemical composition of mineral components in the rock volume.

6. The computer-implemented method of claim 2, wherein the changes to the carbonate pore structure in the rock volume determined by the second set of multiple physical, chemical, biological, and geological processes include generation of porous rocks in the rock volume based on dissolving of areas of carbonate rock in the rock volume.

7. The computer-implemented method of claim 6, wherein the changes to the carbonate pore structure in the rock volume determined by the second set of multiple physical, chemical, biological, and geological processes further include clogging of the porous rocks in the rock volume based on growth of calcium carbonate in the rock volume.

8. The computer-implemented method of claim 2, wherein the first set of multiple physical, chemical, biological, and geological processes that determine the precipitation of carbonate sediment from seawater includes reaction between calcium cations and carbonate anions to form calcium carbonate.

9. The computer-implemented method of claim 8, wherein the first set of multiple physical, chemical, biological, and geological processes that determine the precipitation of carbonate sediment from seawater further includes ocean tide that recirculates sea water to control precipitation of carbonate sediment and sediment deposition.

10. The computer-implemented method of claim 1, wherein the first set of multiple physical, chemical, biological, and geological processes comprises sedimentary precipitation processes.

11. The computer-implemented method of claim 1, wherein the change to the amount of the carbonate sediment in the geographic volume of interest includes a formation of sediment in the geographic volume of interest.

12. The computer-implemented method of claim 1, wherein the stratigraphy comprises a carbonate stratigraphy.

13. A computer-implemented method for estimating reservoir stratigraphy, quality, and connectivity in a geographic volume of interest, the method being implemented in a computer system, the computer system including one or more physical computer processors and non-transient electronic storage, the method comprising:

obtaining, from the electronic storage, geological data corresponding to the geographic volume of interest;

obtaining a framework for sediment deposition using a first set of multiple physical, chemical, biological, and geological processes, the first set of multiple physical, chemical, biological, and geological processes determining precipitation of carbonate sediment from seawater;

generating a representation of sediment deposition by applying the geological data corresponding to the geographic volume of interest to the framework for sediment deposition, wherein the representation of sediment deposition indicates a change to an amount of the carbonate sediment in the geographic volume of interest as a function of position and time due to the precipitation of the carbonate sediment from the seawater, and wherein the representation of sediment deposition indicates a formation of a rock volume resulting from the change to the amount of the carbonate sediment in the geographic volume of interest as the function of position and time, the rock volume including carbonate pore structure;

obtaining a framework for diagenesis using a second set of multiple physical, chemical, biological, and geological processes, the second set of multiple physical, chemical, biological, and geological processes determining changes to the carbonate pore structure in the rock volume;

generating a representation of diagenesis based on the framework for diagenesis and the representation of sediment deposition, wherein the representation of diagenesis indicates a change in porosity and permeability as a function of position and time due to the changes in the carbonate pore structure in the rock volume; and displaying the representation of sediment deposition and the representation of diagenesis on a graphical user interface.

14. The computer-implemented method of claim 13, wherein the first set of multiple physical, chemical, biological, and geological processes is different from the second set of multiple physical, chemical, biological, and geological processes.

15. The computer-implemented method of claim 13, wherein the framework for sediment deposition is based on sedimentary precipitation processes.

16. The computer-implemented method of claim 13, wherein the change to the amount of the carbonate sediment in the geographic volume of interest includes a formation of sediment in the geographic volume of interest.

17. The computer-implemented method of claim 13, wherein the second set of multiple physical, chemical, biological, and geological processes comprises a groundwater circulation representation and a reactive groundwater representation.

18. The computer-implemented method of claim 13, wherein the changes in the carbonate pore structure in the rock volume includes changes in shape, size, and chemical composition of mineral components in the rock volume.

19. The computer-implemented method of claim 13, wherein the stratigraphy comprises a carbonate stratigraphy.

\* \* \* \* \*